US008788214B2

(12) United States Patent
Klein et al.

(10) Patent No.: US 8,788,214 B2
(45) Date of Patent: *Jul. 22, 2014

(54) AUTOMATED SYSTEM FOR THE COMPARISON OF INDIVIDUAL GENOME, TRANSCRIPTOME, PROTEOME, EPIGENOME, AND METABOLOME DATA WITH DATA FROM BONEMARROW DONOR REGISTERS AND BLOOD BANKS, UMBILICAL CORD BLOOD BANKS AND TISSUE BANKS

(75) Inventors: Thomas Klein, Potsdam (DE); Joachim Dudenhausen, Berlin (DE)

(73) Assignee: Cytolon AG, Berlin (DE)

( * ) Notice: Subject to any disclaimer, the term of this patent is extended or adjusted under 35 U.S.C. 154(b) by 33 days.

This patent is subject to a terminal disclaimer.

(21) Appl. No.: 12/934,578

(22) PCT Filed: Feb. 8, 2010

(86) PCT No.: PCT/EP2010/000959
§ 371 (c)(1),
(2), (4) Date: Dec. 20, 2010

(87) PCT Pub. No.: WO2010/089158
PCT Pub. Date: Aug. 12, 2010

(65) Prior Publication Data
US 2011/0112864 A1    May 12, 2011

Related U.S. Application Data

(60) Provisional application No. 61/150,381, filed on Feb. 6, 2009.

(30) Foreign Application Priority Data

Feb. 6, 2009  (EP) .................................... 09075058

(51) Int. Cl.
G01N 33/48 (2006.01)
G06F 19/00 (2011.01)
G06Q 50/22 (2012.01)

(52) U.S. Cl.
CPC .......... *G06F 19/322* (2013.01); *G06F 19/3443* (2013.01); *G06Q 50/22* (2013.01)
USPC ......................................................... 702/19

(58) Field of Classification Search
None
See application file for complete search history.

(56) References Cited

U.S. PATENT DOCUMENTS

| 8,498,882 B2 | 7/2013 | Klein et al. | |
| 2002/0132343 A1 | 9/2002 | Lum | |
| 2003/0154108 A1* | 8/2003 | Fletcher-Haynes et al. | 705/3 |
| 2008/0234945 A1* | 9/2008 | Walk et al. | 702/19 |
| 2011/0257999 A1 | 10/2011 | Klein et al. | |
| 2013/0041680 A1 | 2/2013 | Klein et al. | |
| 2013/0132379 A1 | 5/2013 | Klein et al. | |
| 2014/0032123 A1 | 1/2014 | Klein et al. | |

FOREIGN PATENT DOCUMENTS

| WO | 2005/097190 A2 | 10/2005 |
| WO | 2007/070280 | 6/2007 |
| WO | 2010/089159 A1 | 8/2010 |

OTHER PUBLICATIONS

Majhail et al: "Double umbilical cord blood transplantation" in Current Opinion in Immunology, Elsevier, Oxford, GB LNKD-DOI:10.1016/J.COI.2006.07.015, vol. 18, No. 5, Oct. 1, 2006, pp. 571-575.
INFORMIX: "Informix Guide to SQL—Tutorial—Informix Extended Parallel Server, Version 8.3 Informix—Dynamic Server. 2000, Version 9.2" in Internet Citation, Dec. 31, 1999, Retrieved from the Internet: URL:http://publib.boulder.ibm.com/epubs/pdf/6530.pdf.
Anonymous: "Cord blood forum: Annotated Bibliography—Cell Dose" in Internet Citation, Jan. 20, 2008, Retrieved from the Internet: URL: http://web.archive.org/web/20080120203934 / http://cordbloodforum.org/biblio/v_donorselect/index.html.
Anonymous: "Cord Blood Forum: annotated Bibliography—Multi-Cord Transplants" in Internet Citation May 10, 2008, Retrieved from the Internet: URL: http://web.archive.org/web/20080510110817 / http://www.cordbloodforum.org/biblio/iii_multicord/index.html.
Mathematical Symbols, RapidTables.com: Online Reference & Tools, accessed on Jan. 17, 2014 at http://www.rapidtables.com/math/symbols/Basic_Math_Symbols.htm.
Lee SJ, Kamani N, Confer DL, Principles and tools for selection of umbilical cord blood and unrelated adult donor grafts, Biol Blood Marrow Transplant. Jan. 2008;14(1 Suppl 1 ):112-9.
Wall DA, Chan KW, Selection of cord blood unit(s) for transplantation, Bone Marrow Transplant. Jul. 2008;42(1 ):1-7.
Petersdorf EW, Optimal HLA matching in hematopoietic cell transplantation, Curr Opin Immunol. Oct. 2008;20(5):588-93.
Gluckman E, Rocha V, Donor selection for unrelated cord blood transplants, Curr Opin Immunol. Oct. 2006;18(5):565-70.
Notice of Allowance issued in U.S. Appl. No. 13/147,835 on Apr. 16, 2013.

* cited by examiner

*Primary Examiner* — Anna Skibinsky
(74) *Attorney, Agent, or Firm* — Joyce von Natzmer; Agris & von Natzmer LLP

(57) ABSTRACT

The invention relates to a system for the automatic, rapid and dynamic allocation of biological cells for transplantation, therapy, or research purposes between collection centers or banks (storage sites) and hospitals, transplant centers or research facilities, and for monitoring and supporting the processes from request transmission up to delivery of a cell preparation suitable for allogeneic transplantation, via the use of allocated preparations up to tracking the results in the patient and providing these data for statistical and other purposes, as well as assigning molecular-diagnostic results of individuals with the aim of verifying options—even in advance—of transplantations among the inventory of registers or banks. Using said system, it is possible for the first time—even in advance and online and with automatic retries—to propose complete solutions in the form of transplantations in specific and individual cases.

11 Claims, 5 Drawing Sheets

Figure 1:
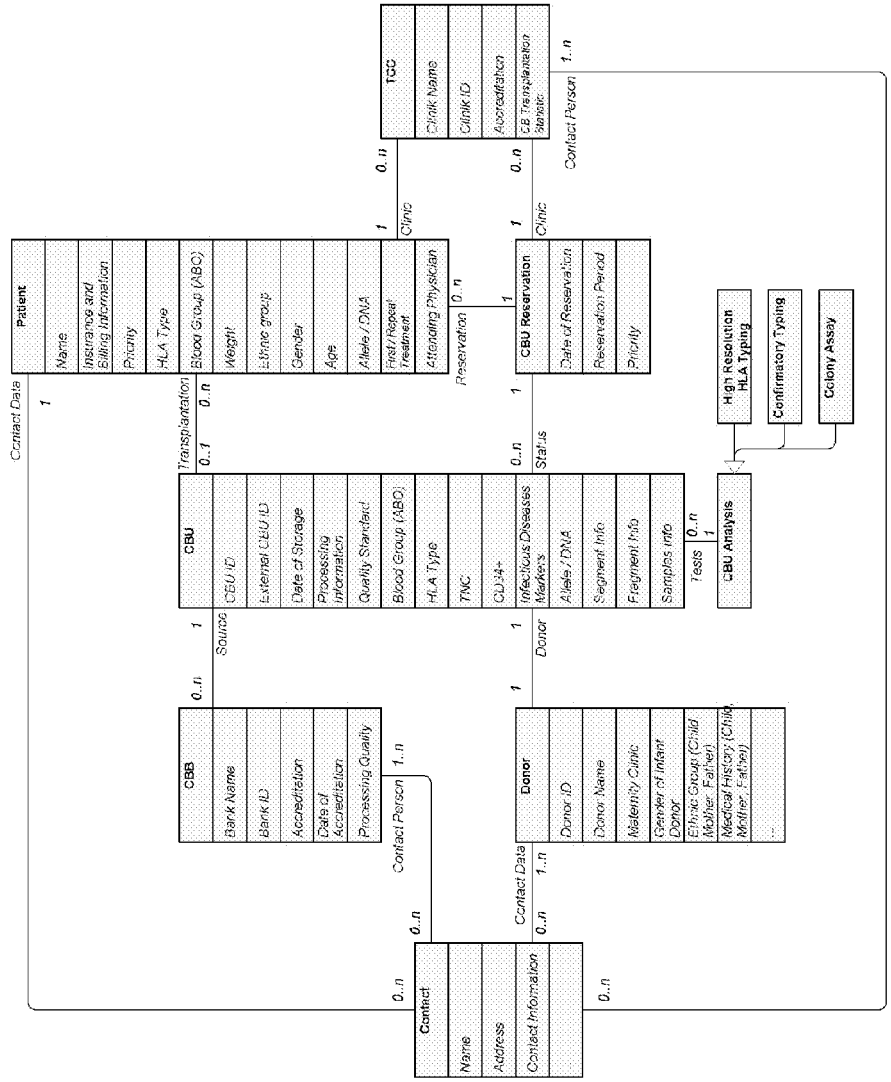

AUTOMATED SYSTEM FOR THE COMPARISON OF INDIVIDUAL GENOME, TRANSCRIPTOME, PROTEOME, EPIGENOME, AND METABOLOME DATA WITH DATA FROM BONEMARROW DONOR REGISTERS AND BLOOD BANKS, UMBILICAL CORD BLOOD BANKS AND TISSUE BANKS

This is the U.S. national stage of International application PCT/EP2010/000959, filed Feb. 8, 2010 designating the United States and claiming priority to European application no. EP09075058.9, filed on Feb. 6, 2009 and claiming the benefit of U.S. application No. 61/150,381, filed on Feb. 6, 2009, which are incorporated herein by reference in their entirety.

The invention relates to a system for automatic, rapid and dynamic comparison of e.g. individual molecular diagnostic or analytical data of genome, transcriptome, proteome, epigenome or metabolome with data from e.g. bone marrow donor files or from umbilical cord blood banks or other banks of stem cells, biological materials or tissues. On the one hand, the system enables individuals—even prior to the onset of a disease as established by their molecular diagnosis—to consider options involving therapy with cells or other stored preparations and substances and initiate therapy at any time. On the other hand, registers or umbilical cord blood banks or other biological databases might use the system to initiate inquiries with providers of molecular services or providers of electronic databases of personal health data, such as Health Vault by Microsoft, as to whether their clients, e.g. those having certain genetic data and other molecular data, would be ready to furnish e.g. umbilical cord blood, so that e.g. the respective inquiring umbilical cord blood bank would be enabled to strategically develop the inventory e.g. for specific HLA types.

Various procedures and methods of allocating umbilical cord blood (UCB) preparations between collection centers and cord blood banks on the one hand and hospitals and transplant centers on the other hand have emerged in recent years. All of these procedures and methods have their origin in processes required in the allocation of bone marrow. However, no automated processes are available as yet. A hospital in need of a UCB preparation intended for a patient/recipient for transplantation would make inquiries with registers as to whether they have a UCB preparation available for their patient that correspondingly complies with a number of biological and medical characteristics. For example, the registered data may relate to the so-called HLA match or to the number of cells present in the preparation, or other medical or biological data (e.g. blood group).

Hospitals and transplant centers have so-called coordinators who perform the selection of a particular UCB transplant with reference to the submitted data. The coordinators suggest a selection of preparations to the attending physician. The physician decides which, if any, transplant will be used. For each preparation, the hospital is required to inquire all important data relating to the respective preparation so as to be able to order the proper cord blood unit. However, no worldwide standards have been defined for information deposited in a so-called Unit Report. Also, no correlation between data of individual preparations has been made as yet. When selecting preparations, coordinators are subject to an iterative process which is time-consuming and prone to error.

This problem is aggravated by the fact that many deposited UCB preparations, although suitable according to e.g. HLA match, are too small for transplantation, i.e. the number of cells in the preparation is insufficient. Clinical research during the past five years has demonstrated that the number of nucleated cells (TC) and cells hereinafter referred to as CD34+ cells (having the capability of hematopoiesis) included in umbilical cord blood is of crucial importance for successful transplantation. With a large number of cells, the genetic fit (HLA match) can be substantially less compared to the HLA match required in bone marrow transplantations. While the required numbers of cells and their correlation with the HLA match have been described in the prior art, they have not been systematically used in established methods as yet. At present, coordinators and cord blood banks are confronted with the problem of identifying matching preparations in individual tests and comparing them with the data of patients. This is all the more difficult because possible preparations are usually distributed over a number of banks and have been described using different methods and standards.

As disclosed in the prior art, e.g. in US 2002/0132343 A1, successful treatment of patients (leukemia, etc.) with matching umbilical cord blood preparations requires a high number of cells and high/guaranteed product quality (including certification by the FDA, etc.) which can be provided in addition to simple and direct use in a transplant clinic. What is described is an integrated system (SCBS) for expanded and matched stem cells (not only umbilical cord blood), which comprises the entire life and production cycles (obtaining source material, production, certified quality assurance, and delivery). The integrated system meets the regulatory quality requirements and standards in accordance with the FDA, etc., such as FACT, CGTP, AAB, and a preparation matching the patient's tissue is selected from an existing (allogeneic) cord blood reservoir. US 2002/0132343 A1 describes that well-known methods for typing (HLA typing of at least six loci) donor and patient cells in compliance with the regulatory standards are to be used. In addition, the use of an automated tracking system for monitoring individual preparations/samples and follow-up is described therein. The donor cells (source material) come from a certified source (cord blood bank) where the relevant information (e.g. TNC, HLA loci, number of CD34+ cells) per sample is collected in accordance with the quality standards. According to US 2002/0132343 A1, the source material is processed in such a way that only relevant cells are processed, and the desired cells (e.g. CD34+ cells) are expanded ex vivo. The stem cell products thus produced are provided for use in the form of a patient treatment kit. They include a defined characteristic and can be used directly by the attending physician. An ordered SCBS product matches at least 4/6 antigens or 3/6 alleles with $2 \times 10^7$ cells/kg for children (<12 years) or patients of <50 kg body weight and $1 \times 10^7$ cells/kg body weight for all other patients. As a central element, US 2002/0132343 A1 describes the ability of direct delivery of SCBS products to transplant centers having ordered the product. To this end, the SCBS products are packed in special containers to be shipped by courier services. This includes attempts of maintaining the quality standards. The SCBS system and the methods described therein do not consider the problems of automated selection of suitable preparations. What is described is the current state of the art of manually selecting stem cell preparations (HLA matching, cell count/weight correlation, etc.). US 2002/0132343 A1 does not show how the time needed to identify a suitable donor material can be reduced or how the manual steps required to select between a number of potentially suitable preparations can be automated.

Further, US 2002/0168639 A1 discloses that, as a result of the limited capacity of the analytical instruments, it is difficult to compare a tissue sample with a large number of comparative samples. US 2002/0168639 A1 describes a profiled substrate which, on the one hand, can receive a sample tissue thereon and, on the other hand, a microarray allowing the use of various comparative samples for simultaneous analysis. The reactivities of test tissue or microarray samples are stored in a database and correlated with other information about the patient from whom the test tissue has been obtained (e.g. age, weight, sex, medical history). The database system disclosed in US 2002/0168639 A1 is connected to an information management system (IMS) capable of performing searches and correlations. This allows comparisons and correlations of biological reactivities between test tissue and samples of the microarray. To this end, the capabilities of state-of-the-art business analytics products for data analysis and visualization, as in "Tibco Spotfire", are utilized. US 2002/0168639 A1 involves obtaining and storing data relating to tissue cells and the donors thereof. These data are compared using standard methods of analysis so as to identify correlations etc. for research or diagnostic purposes. There is no disclosure indicating how to perform a correlation directed to a specific issue. Rather, reference is made to general options reflecting the prior art.

GB 2407193 A describes a system allowing automated performance and evaluation of biological cell line experiments including image analyses. On the one hand, the system is constituted of a unit that allows definition of new experiments and automated performance thereof, the system being open to the effect that any experiment and device can be registered and used in a modular form. The second system component comprises the automated analysis (image analysis) of experiments, the primary aspect mentioned being image analysis of assays, i.e. the results of the assays (the experiments) are fed into the system to be analyzed therein. It is possible to use variable/extensible analytical techniques. The overall system automatically controls the implementation and analysis of multiple successive experiments. The implementation process can be flexibly defined or adapted for this purpose. The results are stored in a database and displayed to the user via flexibly definable reports. GB 2407193 A shows that complete laboratory processes can be automated for cell line experiments. Similar situations are known from industrial practice in many domains of application. GB 2407193 A provides a framework for automated data analysis as part of the process.

US 2004/0121369 A1 addresses the problem of automating the flexible use of a plurality of devices and analytical methods as part of complex biological laboratory experiments. Passing data for assessment successively through various software applications or parallel processing of data as part of changing laboratory processes is a complex matter and requires individual human coordination (manual data formatting or complex individual programming). US 2004/0121369 A1 provides a flexible framework for automation of laboratory experiments and evaluation thereof. The system allows flexible registration (connection) of laboratory equipment controls to be used as part of individually and freely definable experimental operations. Likewise, analytical equipment and software can be flexibly registered and integrated in the overall process. US 2004/0121369 A1 describes a flexible registration mechanism for this purpose, which solves the problem of different interfaces and protocols of devices and analytical applications, so that efficient coupling thereof is possible. The information is stored in a database. US 2004/0121369 A1 addresses the problem of increasing the efficiency in specific processes. As demonstrated therein, working on a problem that previously required manual support by skilled personnel may proceed in an entirely automated fashion. However, the solution to the problem resides in efficient coupling of devices rather than efficient selection of specific cell preparations.

WO 02/077640 A2 discloses a system intended to efficiently process and evaluate large amounts of data arising in connection with the analysis of biomolecules using microarrays and, at the same time, optimize the analytical process. The disclosed automated system allows grouping, e.g. on the basis of physical properties, of large amounts of data in a database using data mining methods and analyzing the results by a self-learning neural network. Using mathematical and statistical methods, the neural network allows automated generation of new samples complying with the desired type of problem. Thus, mathematical and statistical (self-learning) algorithms are used to respond to specific problems with respect to a desired biomolecule. However, the algorithms are not transferable to other systems and can only be used in the above-mentioned system.

US 2008/0014174 A1 describes the methodical production of lymphocyte preparations, the storage thereof, as well as a ready-to-use kit for application in a patient. The lymphocytes are derived from peripheral blood of donors matching with the patient in at least four loci. Certain tumors, viral infections and autoimmune diseases are intended to be treated using HLA-matched allogeneic activated lymphocytes. There are no statements relating to the selection process in detail.

Furthermore, DE 600 30 978 T2 discloses a method which allows simultaneous quantitative high-quality analysis of a plurality of biological samples using a sensor platform. More specifically, the chemical and physical properties of a sample to be analyzed are determined by the sensor platform and introduced into a signal assessment. The system can be used, inter alia, to determine the HLA values of samples.

There is no description in the prior art relating to the exact process of selecting the preparations. It is generally known which parameters should be used at minimum to select suitable preparations, but it is not possible to deduce the "best" preparation from the analyzed preparations. Furthermore, there is no description in the prior art relating to a selection system which selects a suitable preparation and presents the result to the coordinator accordingly and can optionally proceed in an automated fashion. The prior art discloses that the selection of suitable preparations is primarily made on the basis of HLA typing and provides essentially no further criteria.

Also, the prior art does not disclose any solutions to multiple transplantations. This is a solution strategy used in the event that no suitably large preparation can be found. The search problem is then extended to two or more preparations which together include sufficient cells and also have sufficiently matching HLA values both among each other and with respect to the patient.

The object of the invention was therefore to provide a system that does not have the disadvantages of the prior art and allows selection and distribution of a suitable preparation, to which end additional selection criteria should be taken into account.

Surprisingly, the problem is solved by the independent claims. Preferred embodiments of the invention can be inferred from the subclaims.

Quite surprisingly, a system for the allocation and selection of biological cells or tissues, in particular umbilical cord blood preparations, for transplantations, therapies and/or research purposes between at least one collection center and/or or storage site and at least one clinic, transplant center and/or research facility, the latter communicating with each other via wired and/or wireless connections on one or more processing units, especially computers, medical systems, storage devices and/or special processors, and being connected via a network of said multiple processing units by means of which data are exchanged, said system comprising the following steps:

inputting experience data of umbilical cord blood preparations in a computer and storing on a storage medium, inputting inquiry data of a potential recipient or patient and storing the data on a storage medium, said inquiry data comprising genome, transcriptome, proteome, epigenome and/or metabolome data, presetting search criteria, particularly the storage of said search criteria on a storage medium and/or a processing unit, patient search, said search comprising comparing the experience data with the inquiry data, and automatic evaluation of the search being effected, and/or order processing and tracking being effected on the basis of this evaluation, and the umbilical cord blood preparation being ordered via the network, wherein particularly the potential umbilical cord blood preparations are arranged and selected according to HLA match, patient weight, number of nucleated cells (TNC) and number of hematopoietic cells (CD34+) and, in addition, compared with the genome, transcriptome, proteome, epigenome and/or metabolome data, does not have the disadvantages of the prior art.

In the meaning of the invention, a system describes a set of individual technical components which are related to each other and interact. Advantageously, a system may comprise programs and data processing equipment as well as elements such as transport containers, UCB preparations.

In the meaning of the invention, processing units preferably describe input devices by means of which data or information is entered and stored preferably in digital form. The processing units preferably comprise computers, medical systems, storage devices and/or special processors suitable for input and storage.

In a preferred embodiment the processing units can be present separately and/or in various forms of hardware, software and/or firmware. Thus, it can be advantageous if medical systems, such as analyzers, automatically transfer the analyzed data into the system and require no manual input to this end.

In the meaning of the invention, molecular diagnostics describes diagnostics which detects disease-specific biomarkers preferably by means of tailored probes either via imaging methods in the patient's body, i.e. in vivo, or indirectly in collected samples, i.e. in vitro. This may additionally include molecular-biological methods likewise used in the detection of biomarkers. The advantages of molecular diagnostics over standard methods are higher sensitivity and more rapid response.

The teaching of the invention also represents a combination invention in which the above-mentioned elements cooperate to provide a system for the allocation and selection of a biological transplant, wherein—in addition to standard analyses comprising HLA typing—genome, transcriptome, proteome, epigenome and/or metabolome analyses are carried out and the transplants are classified according to these analyses. The effective cooperation of the system components generates a synergistic effect which is characterized in that a single system is available for all the above-mentioned operations, so that all operations can be monitored and controlled by the system both in a central and decentralized manner. All institutions involved in transplantation, comprising hospitals, UCB banks, or physicians, can gain access to the system and monitor the progress of transplantation. The system according to the invention compares the incoming patient data or inquiry data with the data or experience data of registered cell preparations using a multi-level compatibility matrix and varying classification criteria. Advantageously, comparison is fully automatic, and an attending physician can advantageously gain online access to the data. Advantageously, a physician can be automatically provided with proposed solutions as to which single preparation (single transplant) or which intermatching preparations (multi-transplant) are possible for transplantation. In this way, it is possible to fundamentally change and substantially improve the actual advantage of ready-to-use stored UCB preparations compared to lengthy comparative searches performed by coordinators. The system is suitable for all biological, biochemical or chemical materials subject to time-critical allocation in transplantations or other (medical) applications. In a preferred fashion, genome, transcriptome, proteome, epigenome and/or metabolome data of the UCB preparations are entered into the system. To this end, the preparations can be analyzed by service providers, in which event the UCB bank preferably regulates the distribution of samples. The samples are shipped to the service providers where high-resolution analytical methods comprising genome, proteome, transcriptome, epigenome and/or metabolome analyses are used to characterize the UCB preparations in detail. The service providers offer such analyses to non-patients as well. It may be preferred that a non-patient is also allowed to input his or her genome, proteome, transcriptome, epigenome and/or metabolome data into the system, which input is regulated and carried out by the UCB bank or a hospital. The data is stored for future queries.

Characteristic empirical values of the UCB preparations are input via processing units such as computers. It may also be advantageous to automatically analyze a preparation using one or more analytical devices and automatically transfer examined values into a processing unit. For example, UCB preparations can be examined and characterized rapidly and efficiently in laboratory lines which represent a kind of serial arrangement of various analytical devices. The analyzed values are automatically entered into the system and thus rapidly available. Advantageously, the experience data, i.e. the values specific and characteristic for a UCB preparation, is stored on a storage medium. In the meaning of the invention the storage medium, or data memory, is used for storing data or information. Advantageously, the data can be supplemented with additional data at any time and are preferably in digital form. It may be preferred that the storage medium is a mass-storage device preferably having magnetic recording technology or semiconductor memory technology. In the meaning of the invention, a mass-storage device represents a storage medium which stores large amounts of data or information preferably for a prolonged period of time. Advantageously, a mass-storage device with magnetic recording technology can be used, which device writes binary data on the surface of a rotating ferromagnetic disk. In the meaning of the invention, semiconductor memories are data memories consisting of a semiconductor wherein integrated circuits are implemented by means of semiconductor technology. The data are stored in the form of binary electronic switching states in the integrated circuits. This allows permanent and safe storage of the data.

Likewise, the inquiry data are entered into the system by means of processing units and stored on a storage medium. In the meaning of the invention, the inquiry data are data that characterize a particular recipient or potential recipient of the UCB preparations. A potential recipient in the meaning of the invention is an individual having undergone a genome, proteome, transcriptome, epigenome and/or metabolome analysis wherein in particular a predisposition to a disease has been found which can preferably be treated by means of a biological transplantation therapy. The data of the potential recipient can also be present in the system in the form of inquiry data. The inquiry data advantageously comprise genome, transcriptome, proteome, epigenome and/or metabolome data and can be determined by, for example, specialized institutions or companies (e.g. genome sequencing facilities).

In a preferred embodiment the genome data comprise a single (monoploid or haploid) set of hereditary material (i.e. double-stranded DNA) which is present in eukaryotes essentially in the form of linear chromosomes. The genome data are advantageously determined via genome analysis or genome sequencing or genotyping wherein the DNA of an organism, an organ, a tissue, or of cells, is isolated and the sequence of all DNA base pairs is determined. On the basis of this information, a cause-effect relationship between the hereditary information (sequence) and the properties of an organism can be found. Instead of complete chromosomes, it may also be preferred to analyze merely genes and/or DNA from eukaryotes. The system can utilize data from genome or sequencing analyses generated, for example, by analyses of a primary tumor wherein, for example, the genome, epigenome, mutagenome and/or metabolome of the tumor is analyzed, thereby allowing high-resolution statements on the condition of the tumor. Sequencing allows detailed statements on the mutations of the tumor. In this way it is possible to model conclusions as to the origin of the tumor, which in turn is important in prevention and diagnostics. Based on these data it is also possible to estimate the effects of drugs on the tumor and establish an optimal therapeutic regimen, optionally adapted to a particular patient. In many cases the cancer can be treated with stem cells, which in turn depends on the properties of the UCB preparation (TNC content, HLA type, genome analysis). The system can utilize these highly complex data to compare it with a UCB preparation or a tissue or cell preparation. Furthermore, for example, potential recipients whose genome has been sequenced and who have a predisposition to a disease can be registered by the system. If, for example, these potential recipients need a UCB preparation, the genome data of the potential recipient can be compared with those of the UCB preparations by the system. Once a suitable preparation has been found, the system can either store the preparation for the potential recipient or offer an alternative preparation to the recipient. Quite surprisingly, genome analysis of the preparations can substantially improve the search for a suitable preparation. Genome analysis of UCB preparations can also be used to identify genetic and/or chromosomal aberrations in the UCB preparations. Surprisingly, it is possible in this way to substantially improve the efficiency of transplantations because preparations having aberrations, which might be detrimental to transplantation, are shown separately by the system, and only those preparations promising high efficiency are used.

Advantageously, it is also possible to input and store transcriptome data in the system. The transcriptome preferably refers to the entirety of gene transcripts (mRNA) synthesized by an organism under certain environmental conditions. In particular, the developments in DNA chip technology, which allow high sample throughput with small amounts of starting material and high sensitivity, enable extensive transcript analyses. Such a DNA chip, which covers the entire genome of an organism, is hybridized with the mRNA isolated from cells or tissues (or cDNA transcribed therefrom) to identify the transcribed genes. In this way, the expression of specific genes can be determined rapidly and efficiently. For example, the determined expression rate of a gene can provide information as to the activation or deactivation of specific signal transduction pathways, which in turn can be used in the diagnosis or therapy of diseases. Furthermore, it was found that rapid transcriptome analysis of UCB preparations provides comprehensive information as to the condition of the preparations. The data can be used to hierarchically arrange the preparations, which in turn allows surprisingly rapid selection of suitable preparations by the system. The data from the transcriptome analysis can be compared with those from a potential recipient or an actual recipient by the system, thereby allowing a statement as to compatibility.

The proteome data, which can also be entered and stored in the system in the form of inquiry data, comprise in particular the entirety of all proteins in a living organism, a tissue, a cell, or a cell compartment, preferably under precisely defined conditions and at a specific point in time. Analysis and determination of the proteome are performed using proteomics. Proteomics comprises the determination of the entirety of expressed and post-translationally modified proteins under defined conditions with the aim of obtaining statements as to the state of the cell and deciphering complex physiological processes by comparing the protein pattern of a cell or organism under varying conditions. The system is particularly suitable for entering and storing data from phosphoproteomics. Cell growth and differentiation are controlled via a complex network of cellular signaling pathways. Protein kinases play a key role in this context. They transfer phosphate groups to other proteins and thus regulate their enzyme activity. Protein phosphorylation occurs in an estimated 30% of all proteins, representing the most important regulatory mechanism in the control of cellular signaling pathways. In cancer cells, however, certain proteins exhibit massively increased phosphorylation levels. Such over-activation of signaling pathways is characteristic of cancerous diseases. In addition, it was found that changes in protein activity essentially due to phosphorylation also occur in association with transplantations. Phosphoproteomics aims to quantitatively detect all cellular protein phosphorylations in cell and tissue samples, to which end the use of most recent mass spectrometric methods is indispensable. To allow quantitative statements as to the phosphorylation level, the proteins of cellular states to be compared (e.g. with and without active substance) can be labeled with isotopes distinguishable in mass spectrometry. Prior to the actual mass spectrometric analysis, the phosphorylated proteins can first be cleaved enzymatically into peptide fragments and accumulated using special chromatographic procedures. The precise masses of the phosphopeptides and their characteristic fragment masses resulting from collisions with gas molecules can subsequently be determined in a mass spectrometer. Using bioinformatic methods, it is now possible from the measured results to image the measured phosphopeptides on protein sequences and deduce the relative quantitative changes between the analyzed samples. Advantageously, the system is capable of analyzing in particular UCB preparations preferably using phosphoproteomics. This can be utilized to determine the activation of individual proteins or signal cascades. Also, potential recipients can be characterized by means of proteome analysis, in particular phosphoproteomics. As a result, the system is able to diagnose a disease and find and order an appropriate UCB, tissue and/or cell preparation at an early stage.

Furthermore, metabolome data can be entered into the system. In a preferred fashion this involves the entirety of cellular metabolites, i.e. chemical (usually low molecular weight) substances produced in metabolic reactions. Advantageously, flow or turnover rates of certain metabolites, the metabolite levels and enzyme activities of individual metabolic pathways and/or compartmentalization of various metabolic pathways can also be determined within an organism, an organ, a tissue, or a cell. Advantageously, the system is able to make direct use of data from metabolome analyses. In metabolome analyses (metabolomics), small chemical or biological molecules, i.e. metabolites, are detected and quantified. To this end, various samples can be used, comprising blood plasma, blood serum, urine, CSF, cell extracts, or tissue. The samples are characterized using state-of-the-art analytical methods, such as spectral analysis, mass spectroscopy and/or chromatographic methods, and the biological and/or biochemical interaction with other molecules is modeled. In this way, the molecule can be classified as belonging to one or more signal cascades or metabolic pathways. In addition, the metabolites can be used to determine the effect of drugs on metabolic processes or quantify the influence of a tumor on metabolic activities. In this way, clinical studies can be supported in a simple manner, the data being generated can likewise be entered into the system and compared e.g. with empirical values, so that a suitable cell, tissue or UCB preparation can be found.

Advantageously, epigenome data can also be input into the system according to the invention and analyzed and utilized therein. Epigenetic changes describe changes in the activity of genes that are not related to the sequence level (such as mutations, etc.). The major mechanisms of epigenetic changes are related to chromatin which can be restructured and remodeled in a specific manner. For example, the changes of chromatin may proceed via processes comprising methylation or acetylation of individual chromatin elements. DNA methylation is a strictly controlled biological process supporting the natural regulation of genes and the stability of the genome. Cytosine can be modified by attaching a chemical methyl group. In general, DNA methylation in gene regulatory regions (i.e. gene promoters) silences the respective genes either by directly preventing binding of transcription factors or by allowing condensation of chromatin. Different cells switch off different genes, so that each cell type has its specific "DNA methylation fingerprint". This fingerprint undergoes specific changes particularly during aging and in the presence of diseases and therefore represents a source of biomarkers for organ-specific diagnosis and classification of diseases. For example, cancer-specific DNA methylation patterns can be used to draw conclusions about the gene activity on the basis of the methylation patterns. Advantageously, the methylation patterns can be determined using non- or minimally invasive methods, so that varying activity of genes can be detected at an early stage. Furthermore, DNA methylation can be quantified easily because the non-methylated copy of the same gene can be used as internal reference in the sample. DNA methylation is not affected by sample processing in clinical routine, so that it can be analyzed in tissue samples fixed and embedded in paraffin for histological analysis by a pathologist. Methylation of cell or tissue samples can readily be determined in high-throughput analyses, such as microarray technology or PCR or sequencing technologies. Quite surprisingly, the system can provide statements as to the compatibility of UCB preparations with a recipient on the basis of epigenome analysis. Surprisingly, epigenome analysis of UCB preparations and analysis by the system results in a significant reduction of transplant rejection responses.

In the meaning of the invention the epigenome describes the entirety of epigenetic characteristics, i.e. all meiotically and mitotically heritable changes in gene expression that are not encoded in the DNA sequence itself.

It can also be advantageous to enter and store mutagenome data in the system.

The system is particularly advantageous in the field of oncology in view of the large amounts of data arising therein which must be processed and managed. The system allows interaction, as an integrated platform, between hospitals, cell, tissue or UCB banks, as well as institutions or firms having the capacity of high-resolution analysis. The system can easily manage large amounts of data and also allows input and/or storage of different formats. Surprisingly, it was found that, by using the system, different file formats arising e.g. in genome analysis (sequencing) can be stored in a compressed form in the system and are nevertheless compatible with other datasets. That is, a UCB bank or hospital linked via the system can gain access to the highly complex data and start a query because the system provides a uniform data format. In this way, highly complex data can be managed easily and efficiently by the system. The system also permits rapid and automatic searches according to preset parameters.

Advantageously, the inquiry data can be entered into the system immediately during acquisition, and this process preferably proceeds automatically. For example, the data can be transferred into the system after successful genome sequencing. To this end, the system offers suitable data storage means capable of processing various data formats. Advantageously, different data formats are processed into a uniform and comparable format. This is a substantial advantage over databases or data management programs described in the prior art because easy and, above all, rapid exchange of data is possible for the first time.

Advantageously, data relating to patients and preparations (e.g. HLA values or weight and cell number) are correlated by information-processing systems and utilized for the evaluation of matches. Advantageously, the data relating to available umbilical cord blood preparations (UCBP) are provided and updated locally by the blood banks. The data relating to the available UCBP inventory are collected e.g. in a repository (database) and provided for searches therein.

Once the data, i.e. experience data and inquiry data, have been entered and stored in the system, the system can be searched for a match using default search criteria. During the search, the experience data are compared with the inquiry data, and an automatic evaluation of the search is displayed to the searcher. It may also be preferred that the system automatically performs a search at regular or irregular intervals and transmits the search result to the searcher (comprising a hospital or UCB bank). Advantageously, the search result, or the evaluation, can be output hierarchically. For example, hits revealing complete match with the search criteria may be rated higher, or weighted differently, than those where complete match is absent. In this way, the results can be displayed clearly, and the searcher can obtain an overview of the outcome more easily. In a preferred fashion the evaluation of the search result proceeds automatically and can be adapted manually by the searcher using different weighting of search criteria.

The recipients or the clinics responsible for the recipients can precisely define the criteria according to which the search for a match is to proceed. To increase the efficiency and minimize errors, the search parameters used in weighting and automated selection can be stored centrally for attending physicians and hospitals, for example. Thus, the default search parameter sets can be fetched at the beginning of a search and optionally modified by an expert (expert mode). Advantageously, the search for suitable UCBP proceeds automatically but can also be performed step by step or checked by a person skilled in the art.

Based on an evaluation of the search, the UCB preparation can be ordered from the cord blood bank or hospital. Advantageously, the order is placed via the network and can thus proceed over a long distance without requiring contact with the respective bank. To this end, the processing units and/or storage media are equipped with data transmission units known in the art, which enable fast data transfer. Examples include DSL, ISDN or other connections that can be used for communication between processing units. To prepare order processing, interaction with a blood bank can be advantageous to arrange further or missing investigations. Up to now, this has been a manual and time-consuming step. Advantageously, the system supports the processes via automated workflow, i.e. a working process that proceeds in a predefined sequence of activities within an organization. The workflow continuously informs about pending orders and the status of individual orders, thereby improving the quality of the results and making the processes per se more efficient and rapid. When tracking the delivered and transplanted preparations, the system is able to gather information required in medical and pharmacological terms. In a preferred embodiment the system can also automatically create statistics relating to the processing speed and the rapidity of blood banks, as well as success statistics depending on types of disease and UCBP parameters. Thus, a system user, e.g. a coordinator, is provided with a clear representation of handling and, using the latter, can optionally improve working processes, e.g. order processing, because he or she obtains useful evaluations of, for example, the blood bank.

Quite surprisingly, the potential UCB preparations can be arranged and selected according to HLA match, weight of patient, number of nucleated cells (TNC), and number of hematopoietic cells (CD34+) and compared with the genome, transcriptome, proteome, epigenome and/or metabolome data. That is, genome, transcriptome, proteome, epigenome and/or metabolome data preferably of the UCB preparation and of a potential recipient, or recipient, are analyzed, the results of the analysis preferably being entered into the system and preferably stored on a storage medium. Thus, the query for a suitable preparation by the system can preferably be based on the genome, transcriptome, proteome, epigenome and/or metabolome data and HLA match, weight of patient, number of nucleated cells (TNC), and number of hematopoietic cells (CD34+). Advantageously, it is possible to process in particular the highly complex file formats of genome, transcriptome, proteome, epigenome and/or metabolome analyses by means of said system. This is a substantial progress as it makes searches for suitable UCB preparations more rapid and efficient and establishes data exchange between collection center, storage site, clinic, transplant center and optionally research facilities. Nothing of the kind has been described in the prior art.

It was not predictable from the prior art that such different data formats could be processed and evaluated by a single system. This is a substantial progress and solves a long-standing problem. In addition, data from bone marrow donor files or umbilical cord blood or other banks of stem cells, biological materials, or tissues can be used and compared with the genome, transcriptome, proteome, epigenome and/or metabolome by the system. A system is available for the first time which is able to interlink different data and performs automatic searches and informs e.g. a clinic about the existence of a suitable preparation.

A system is now available to professionals, which allows direct use of results of a molecular analysis arranged by a user prior to a particular disease, such as genome sequencing, and comparison with existing data sets. This involves considerable advantages in transplantation medicine because costs for extensive diagnostic investigations in cases of disease do not arise, and data pools already existing or to be created, or single sets of data (e.g. of metabolome, epigenome, proteome, transcriptome or genome) can be used to this end without time delay. In this way, considerable amounts of data are available to physicians and hospitals, allowing comprehensive evaluation and diagnosis. Not only safer transplantation and therapy but also prevention is possible in this way, which in turn saves money in public and private health insurances as costly and extensive preventive medical examinations can be replaced by low-cost high-throughput analyses and molecular diagnoses. By virtue of the system, individuals are able—based on their molecular diagnosis and even before the onset of a disease—to consider options of a therapy with cells or other stored preparations and substances and initiate therapy at any time. On the other hand, registers or cord blood banks or other biological banks can use the system to launch inquiries with providers of molecular services or providers of electronic databases including personal health data, such as Microsoft's Health Vault, as to whether their clients, e.g. those having specific genetic and other molecular data, would be ready to donate e.g. umbilical cord blood, so that e.g. the respective inquiring cord blood bank could strategically develop the inventory for e.g. specific HLA types.

By virtue of the system, individuals or families are able for the first time, e.g. on the basis of "genotyping" or molecular-diagnostic examinations and evident risk profile of particular diseases such as leukemia, to examine—even beforehand—whether a matching bone marrow or blood or tissue donor, or a suitable allogeneic umbilical cord blood preparation, or a suitable stored allogeneic preparation of other origin, such as fatty tissue, is available worldwide. Thus, with respect to regenerative medicine, an individual or family can implement a health strategy as a preventive measure by checking in advance, e.g. after a genetic predisposition to a disease has become evident, if a potentially life-saving preparation or a donor is available.

As a result of such early awareness of inherent risks, e.g. from genome analysis and an overview of potential genetic fit to potential donors or stored preparations, individuals or families in their life planning can also make sure in a highly economic manner that e.g. umbilical cord blood of their children is collected at birth, processed and stored, so that, as a consequence, there is a high probability (about 20-25%) that the umbilical cord blood is available as a transplant for high-risk members of the family.

Also, it can be advantageous if allogeneic storage of umbilical cord blood is free of charge in those cases where the preparation is donated and the storage bank guarantees return of the preparation or delivery of a similar preparation, if required. In this way, costly and medically controversial autologous storage can be avoided because the respective umbilical cord blood is provided to an inventory or register wherein possible substitute preparations are stored in sufficient quantity.

From the perspective of a bone marrow register or a cord blood bank, the system can be used to identify—e.g. with genotyping providers—rare or frequently or urgently needed HLA typings lacking or under-represented in their own inventory. By virtue of the system, strategic and well-planned supplementing and consolidation of the inventory of a bone marrow register or a cord blood bank in terms of HLA typing and other features, e.g. alleles or results from molecular-diagnostic methods, are possible for the first time.

The invention is new and involves inventive activity as it discloses a system for the automatic management and order placement of UCB preparations and their hierarchical arrangement according to defined factors, which system enables integration of inquiry data determined in particular by high-throughput analyses or molecular diagnostics. The system differs distinctly from the prior art. Likewise, the integration of data determined e.g. by genotyping or by means of metabolomics, epigenomics, phosphoproteomics or genomics was not obvious to a skilled person from the prior art, but was a complete surprise. Nothing of the kind has been described in the prior art. The use of these data opens up a completely new technical field to those skilled in the art. In general, the prior art merely discloses standard analyses of samples following transplantation (e.g. blood analysis), with no genome, proteome, transcriptome, epigenome and/or metabolome analyses being carried out to characterize e.g. UCB preparations or recipients. Owing to the genome, proteome, transcriptome, epigenome and/or metabolome analyses, it is possible for a potential recipient for the first time to make a preliminary inquiry to the system according to the invention to identify potential UCB preparations. In a preferred fashion the preparations are likewise characterized by genome, proteome, transcriptome, epigenome and/or metabolome data, so that the system of the invention can perform a comparison with the data of the potential recipient. Surprisingly, the system can find potential preparations rapidly and efficiently in this way. In addition, characterization of the UCB preparations by genome, proteome, transcriptome, epigenome and/or metabolome data is much more detailed compared to standard analysis. The data not only encompass genetic or chromosomal aberrations, but also methylation patterns, expression of e.g. oncogenes or tumor suppressor genes, and metabolites. This allows comprehensive description of the preparations, and incompatibilities can be identified at an early stage and avoided, so that the transplantation efficiency is substantially improved.

When inputting the data, i.e. the experience data, it is preferred that in particular all UCB preparations registered in the system and stored in various UCB banks and collection centers worldwide are acquired as parameters in an advantageously uniform data set (Unit Report). Inter alia, the parameters comprise:

- Name and identification of the UCB storage bank
- Status of the UCB storage bank with regard to international certifications (e.g. FACT)
- Process reliability of the UCB bank according to classification
- Contact in the respective bank, including contact data
- Identification number of preparation
- Medical history of mother, child and family according to anamnesis form of the maternity clinic
- Ethnic group of mother, father and/or child
- Sex of child
- Date of initial storage of preparation
- Details of preparation processing
- Blood group of preparation
- HLA type of preparation
- Cell count (TNC) of preparation
- Cell count (CD34+) of preparation
- Viral status of preparation
- Allelic characteristics of preparation and/or
- Parameters of molecular diagnostics and analysis said data set being stored on a storage medium and/or processing unit. Advantageously, the combined parameters are input into the system and surprisingly allow unambiguous characterization of a umbilical cord blood preparation (UCBP) because, as a result of the entered data or combination of parameters, each preparation is defined by its specific properties or parameters. Advantageously, this is achieved by combined acquisition of the parameters. Quite surprisingly, the combination of parameters results in a particularly good solution to the object of the invention. In the meaning of the invention, a parameter describes a characteristic quantity, i.e. a characterizing property, that is inserted in the system in the form of data. Advantageously, the data comprise operational details (attributes) of patients, hospitals, physicians, donors, blood banks, UCB preparations (laboratory values, physical and informational properties), order and process information and controlling information comprising search/exclusion criteria, thresholds, weighting factors. The parameters of molecular diagnoses and analyses preferably comprise the quantities of biomarkers specific to certain diseases. In this way, the system can provide rapid statements relating to the activities of metabolic pathways which might be detrimental to transplantation.

Parameters used to characterize the preparations are acquired. In particular, the advantageous combination of parameters has not been described in the prior art and allows unambiguous assignment and acquisition of a preparation. Thus, a database—a UCBP database in the meaning of the invention—can be created, wherein the parameters are stored.

The parameters can be input locally, e.g. by the UCB bank, and the latter can also maintain and update the database. Advantageously, the data can be entered later by the system. On the other hand, the data can also be supplied by external service providers. This is advantageous because clinics or UCB banks need not perform costly and complex analyses by themselves, so that resources can be saved. For example, service providers can be automatically provided with samples by the system prior to transplantation, and the generated data are entered into the system and accessible to all those involved.

In addition to information relating to the UCB bank, such as name and identification of the UCB bank, the bank's status with respect to international certifications (e.g. FACT: "Foundation for the Accreditation of Cellular Therapy") is stored, thereby ensuring compliance with defined standards regarding the quality of preparations. Advantageously, a contact person in the respective bank can also be entered together with contact data. For example, a contact can be an attending physician, or a coordinator responsible for maintenance of the database in the bank. Furthermore, a system-standardized identification number (ID) is preferably assigned, which allows unambiguous assignment. Moreover, comprehensive searches for preparations from the UCB bank can be performed. In addition, process reliability details for each cord blood bank are automatically collected by the system and included in the search. Furthermore, data relating to the medical history of mother, child and family are included in the database according to an anamnesis form of the maternity hospital. Advantageously, this allows assessment of the preparations with respect to specific diseases such as hereditary diseases. The ethnicity of mother, father and/or child is beneficial as information because specific genetic variations may be associated with the ethnic background and might therefore complicate a transplantation. Advantageously, parameters such as blood group, HLA type, cell count (TNC: total nuclear cells and CD34+), viral status, genome, metabolome, transcriptome, proteome and/or epigenome data and allelic characteristics of the preparations are also entered into the database. This comprehensive information allows characterization and identification of preparations and, accordingly, optimum assignment of a recipient.

Advantageously, the data set of each preparation includes information as to whether the preparation has been frozen in segments (if so, how many) and with fragments (if so, how many) and with DNA samples (if so, how many). Fragments, segments and samples are used in a subsequent detailed determination of the preparation with respect to a particular patient and to check key data prior to transplantation. The system provides information as to how many segments, fragments and DNA samples are available at the time of inquiry and/or which further tests, such as CT (confirmatory typing) HR (high-resolution HLA typing), sequencing, genotyping, or CA (colony assays) have already been carried out, and/or what the results of these tests were. In addition, the status of a preparation is recorded, i.e. if and from what time on the preparation has possibly been reserved by a clinic.

In the meaning of the invention the database comprising the data or parameters may also be referred to as data warehouse, i.e. a central data collection, the content of which is composed of data from different sources. The data warehouse not only manages all data of the individual preparations in each of these UCB banks, but also dynamically matches each inserted preparation with all other preparations in the various UCB banks, thereby automatically documenting upon registration of each preparation which combination of preparations can be used for potential subsequent double or multiple transplantation (multi-cord).

The first classification criterion for such a multi-cord match between registered preparations is the HLA match, but it may also be preferred that the first classification criterion is the blood group or the TNC count. Matching is preferably present in at least four out of six HLA features, and those preparations having the most HLA matches are at the top in the order of suitability as multi-cord. Alleles and the results of molecular diagnoses and analyses from genome, transcriptome, proteome, epigenome and metabolome are possible as further classification criteria. Surprisingly, it was found that risk patients and incompatible UCB preparations are rapidly identified by the system on the basis of genome, transcriptome, proteome, metabolome and/or epigenome analysis. That is, UCB preparations and potential recipients, or recipients, are analyzed with respect to genome, proteome, epigenome, transcriptome and/or epigenome data, and the generated data are compared by the system. The system is able to calculate incompatibilities and provide a clear representation thereof. Certain characteristics increasing the risk of rejection can be identified by analyzing these data. Early recognition of such a risk, i.e. prior to transplantation, can avoid incompatible preparations during selection. If no alternative preparations are available, early onset of therapy can reduce or even completely suppress a rejection response. Surprisingly, owing to the classification criteria, particularly the genome, proteome, metabolome, epigenome, and/or transcriptome analyses, the system is able to use only fully compatible UCB preparations for transplantation.

In the meaning of the invention, classification describes a defined order of elements. Classification of the elements can be related to their properties, e.g. the parameters or attributes (for example, UCB preparations). In the meaning of the invention the classification criteria describe the way in which the classification is created (for example, all UCB preparations according to their TNC size from the largest down to the smallest preparation). Advantageously, it is possible to apply filtering criteria to a classification, which means that, for example, only those preparations having a defined TNC size are included in a search. It is particularly advantageous that, in the event of relatively large amounts of data, these classifications can be used as index to perform e.g. efficient searches (also as a combination using a number of criteria).

The second classification criterion is blood group or HLA type equality or compatibility. Again, preparations with blood group/HLA equality are on top, followed by those having compatibility, and blood groups excluding each other result in non-suitability as multi-cord with respect to certain other preparations.

Cell count (TNC and CD34+ or CD133+), ethnicity and allelic characteristics or e.g. certain metabolic, proteomic, epigenetic or other genetic properties are carried along as information or characteristics of the preparations and used to determine the further order, i.e. if the preparations would be suitable and if it would be advantageous to examine another feature of the preparations. Again, preparations with high TNC count and e.g. high CD34+ or high CD133+ cell count are higher up. The same applies to identical ethnic origin and compatible allelic characteristics. Hence, possible pairings or groups of matching preparations are identified and ranked in the data stock of the system, i.e. the data present in the database, even prior to inquiry by a clinic for an individual patient.

In a preferred fashion the inquiring hospital performs a patient search wherein the determination of patient-compatible preparations comprises the following classification and/or exclusion criteria:

Name and ID of clinic or transplantation center
Names of coordinator and attending physician, including contact data
Status of clinic with regard to international certifications (e.g. FACT)
Average number of UCB transplantations in the inquiring clinic during the last three years
Name of patient, insurance number and other accounting information
Patient's medical history
Indication and therapy proposal of attending physician
Urgency according to defined classification
HLA type of patient
Blood group of patient
Weight of patient
Ethnic group of patient
Sex of patient
Age of patient
Known allelic characteristics of patient and/or data of DNA typing
First treatment or re-treatment said classification and/or exclusion criteria being stored on a storage medium and/or processing unit.

Quite surprising in this context is the option of carrying along genetic aberrations or mutations and various patterns of molecular diagnoses from genome, transcriptome, proteome, epigenome and metabolome in the form of classification or exclusion criteria, the latter also being collected subsequently. That is, it can also be advantageous to classify the preparations according to the properties of genome, transcriptome, proteome, epigenome, and/or metabolome. These properties comprise, for example, mutations, expression of specific genes, presence/absence of specific proteins, methylation of specific genes or chromatin sections and/or conversion of specific metabolic products. Collecting these data allows surprisingly unambiguous characterization of the preparations by the system and, advantageously, comparison with the data of a recipient or potential recipient. For example, such a comparison can reveal incompatibility at an early stage, which might give rise to an increased transplant rejection response. In addition, the system can perform an automated search for suitable preparations and inform e.g. the hospital if a preparation is available. Advantageously, the system reserves the preparation and does not display it to other searchers. Owing to the detailed analysis of UCB preparations and potential recipients, or recipients, by the system, unexpectedly occurring rejection responses or complications during transplantation can essentially be avoided because only those preparations matching in essential criteria with the analyzed characteristics of a potential recipient, or recipient, are transplanted.

Owing to the advantageous combination of classification and/or exclusion criteria, which have a synergistic effect in combination, a patient can be unambiguously characterized, in which context it is advantageous to compare the data of a patient with stored data of a preparation in a UCB bank. The synergistic effect is that the inventive combination of classification and/or exclusion criteria, e.g. genome, proteome, epigenome, transcriptome and/or metabolome analyses by means of the system, allows much more precise characterization of the preparations. Surprisingly, it was found that suitable preparations are found more rapidly when using the system because a relatively large number of characteristic features are available and no further investigations with respect to compatibility must be carried out. This results in a reduction of work and cost. Moreover, rapid retrieval of a suitable preparation is of paramount importance for successful transplantation. Advantageously, patient and preparation are characterized using the same criteria, so that direct comparison is possible. Advantageously, the properties of the preparations can be compared with those of a patient using e.g. a compatibility matrix in several stages and various classification criteria. The compatibility matrix allows direct and easy comparison of the properties of the preparations with those of a patient and provides information as to whether the preparation is tolerated by the patient. Advantageously, a number of results, i.e. preparations, that would be optimal for a patient are presented to the attending physician. Advantageously, it is also possible to propose preparations for single-cords or multi-cords with regard to transplantation in a particular patient. The final decision as to which preparation or preparations should be used can advantageously be made by the attending physician.

In the meaning of the invention the criterion of indication and therapy proposal of the attending physician describes the diagnosis, analysis and indication of the disease from which the patient is suffering (e.g. acute myeloid leukemia (AML) or ischemic stroke) and for which the attending physician suggests a particular treatment (therapy). The therapy proposal comprises, among other things, settlement of the product to be used (e.g. umbilical cord blood preparation in the form of a finished drug), date, course and duration of treatment, as well as number, dosage and administration of product(s) and possible measures in case of relapse.

Furthermore, in the meaning of the invention the criterion of urgency according to a defined classification describes prioritizing the search and assigning a suitable preparation for a particular patient versus a parallel search performed for another patient, which patients might possibly use the same product because of their genetic typings, said prioritizing representing a compulsory settlement to all users of the database or platform. The classification table can be set by a coordinator and is based on the medical urgency with which a patient requires the preparation.

Advantageously, the parameters important e.g. for a particular patient and, as a consequence, important to the search for a suitable preparation can be predefined by the attending physician or the hospital prior to search, so that efficient and automated search processing is possible.

For example, information relating to the treating hospital is not only logged for process quality assurance but also collected as necessary information in advance, without which the search process cannot be started. Furthermore, the preferred embodiment automatically collects statistics for each hospital relating to number and type of transplantations, so that the assessment of a clinic with respect to suitability for transplantation is easier. In this way, clinics having little or no experience with transplantations can be excluded very easily.

The urgency of a case, e.g. a transplantation, is accounted for when prioritizing preparations in cases of conflict. The option of resolving potentially occurring conflicts with respect to reservation and ordering of UCBP is advantageous to the automation of operations. Inter alia, the prioritization information can be used to this end. It is also advantageous to collect details required for automated accounting. Particularly in automated mass processing, this is a mandatory precondition and significantly simplifies automation and implies a substantial reduction in working steps.

Advantageously, details or lists of suitable preparations can be retrieved at each level during the preferred automatic selection of a suitable preparation. This allows a clear view on the selection for a coordinator or skilled person performing the search.

In a preferred fashion the classification of potential umbilical cord preparations is set as follows:

$ML_{prep}$=match level according to HLA match between preparation and patient $$ML_{Prep} := \begin{cases} 6: HLA_{Prep} \text{ and } HLA_{Pat} \\ \quad \text{match in 6 out of 6 values and blood group compatibility} \\ 5: HLA_{Prep} \text{ and } HLA_{Pat} \\ \quad \text{match in 5 out of 6 values and blood group compatibility} \\ 4: HLA_{Prep} \text{ and } HLA_{Pat} \\ \quad \text{match in 4 out of 6 values and blood group compatibility} \\ \text{Preparation not included: other} \end{cases}$$

$CF_{prep}$=cell factor defines the required number of cells per kg of patient weight at corresponding match level $$CF_{Prep} := \begin{cases} 3 \times 10^7 : ML_{Prep} = 6 \\ 4 \times 10^7 : ML_{Prep} = 5 \\ 5 \times 10^7 : ML_{Prep} = 4 \end{cases}$$

$CN_{prep}$=classification number of a preparation allowing arrangement of preparations in accordance with TNC and match level $$CN_{Prep} := \frac{TNC_{Prep}}{CF_{Prep}}$$

$SL_{Single}$=short list of preparations to be considered for single transplants $$SL_{Single} := \left\{ p \in Prep \,\middle|\, \frac{CN_p}{BW_{Pat}} \geq \frac{1}{\text{kg}} \land ML_{Prep} \geq 4 \right\}$$

The standard classifications of preparations in a short list are made according to the following criteria:

Classification 1=initial ranking according to match level, followed by classification number, followed by CD34+

$$\text{Classification 1}(SL) := \left\{ p1 \in SL, \right.$$

$$p2 \in SL \left| \begin{array}{l} \text{either } ML_{p1} > ML_{p2} \\ \text{or } ML_{p1} = ML_{p2} \wedge CN_{p1} > CN_{p2} \\ \text{or } ML_{p1} = ML_{p2} \wedge CN_{p1} = CN_{p2} \wedge CD34_{p1} \geq CD34_{p2} \end{array} \right.$$

Classification 2=initial ranking according to classification number, followed by match level, followed by CD34+

$$\text{Classification 2}(SL) := \left\{ p1 \in SL, \right.$$

$$p2 \in SL \left| \begin{array}{c} \text{either } CN_{p1} > CN_{p2} \\ \text{or } CN_{p1} = CN_{p2} \wedge ML_{p1} > ML_{p2} \\ \text{or } CN_{p1} = CN_{p2} \wedge ML_{p1} = ML_{p2} \wedge CD34^+_{p1} \geq CD34^+_{p2} \end{array} \right.$$

wherein
Prep=umbilical cord blood preparation
Pat=patient
$HLA_{Pat}$=HLA values of patient
$HLA_{Prep}$=HLA values of preparation
$TNC_{Prep}$=number of nucleated cells of preparation
$BW_{Pat}$=body weight of patient in kg
$CD34+_{prep}$=number of CD34+ cells of a preparation Accordingly, the preferred embodiment is also a combination wherein the above-mentioned elements cooperate to achieve an overall technical success, thereby creating a synergistic effect which is reflected in a surprisingly efficient and rapid search for adequate preparations. Therefore, the classification criteria in the meaning of the invention may also be referred to as search criteria. Advantageously, the search can be performed automatically, so that the search can proceed much faster and errors by individuals involved in the search do not occur. Advantageously, standardizing the search process and combining the classification criteria allows automated mass processing. It may also be preferred to prioritize the preparations according to other classification criteria, for instance according to mutations in a specific gene or according to blood group. It may also be preferred to set the classification of preparations with reference to genome, proteome, transcriptome, epigenome and/or metabolome data, which data are based on high-throughput analyses and/or molecular diagnoses. Thus, for example, it is possible by means of the system to directly sort out or separately list preparations which have an increased concentration of a biomarker and allow conclusions as to increased or reduced metabolic activity incompatible with the characteristics of a recipient. In this way, genetic defects possibly implying an increased risk of rejection can be recognized by the system prior to transplantation. In addition, a potential recipient revealing a predisposition for a disease on the basis of such an analysis (e.g. a genome analysis), which disease can be treated e.g. by means of a UCB transplantation, can perform an inquiry via the system and receive a list of suitable preparations on the basis of the above criteria. Suitable preparations or similar, comparable preparations can be stored in the system and optionally reserved for the potential recipient. For example, the potential recipient may also store umbilical cord blood of one of his of her children in a UCB bank and optionally resort thereto if the defined search criteria match.

The search for a suitable specimen proceeds in several steps. The first step is a basic search. According to an exclusion principle, a so-called "long list" advantageously includes a ranking of all those preparations which match in at least four out of six HLA typings and do not exclude each other with respect to their blood group affiliation, i.e. the result is a match level in accordance with the HLA matches between preparation and patient. At this point in time, the clinic can also import preparations from non-registered UCB banks in the basic search. It may also be preferred to establish the ranking of the long list on the basis of genome, proteome, transcriptome, epigenome and/or metabolome data.

The next step is an advanced search wherein a two-part short list can be utilized with advantage. The list advantageously comprises possible single transplants (single-cord view). This involves preparations possible as single transplant with respect to correlation of the classification criteria of HLA match, patient weight, number of so-called nucleated cells (TNC), and number of hematopoietic cells (CD34+). It may also be advantageous to classify and arrange the preparations on the basis of genome, proteome, transcriptome, epigenome and/or metabolome data. The correlation is based on the following characteristic values: given an HLA match of six out of six, the patient requires e.g. at least $3.0 \times 10^7$ TNC/kg body weight of the patient, i.e., if the patient has a body weight of e.g. 55 kg, the preparation may have a total of at least $1.65 \times 10^9$ nucleated cells. Given an HLA match of five out of six, the same patient requires e.g. at least $4.0 \times 10^7$ TNC/kg body weight, so that the preparation may have at least $2.2 \times 10^9$ TNC if the patient's weight is e.g. 55 kg. Further, given a match of 4 out of 6 HLA types, the preparation may have at least $5.0 \times 10^7$ TNC/kg, i.e. a total of $2.75 \times 10^9$ TNC. Thus, rankings of the identified preparations can advantageously be established according to e.g. two selectable criteria: 1) highest HLA match, followed by highest relative cell number; or 2) highest relative cell number, followed by highest HLA match. If the identified preparations are equal in their positioning, further ranking of the preparations is determined by the level of the CD34+ cell count.

Owing to the preferred embodiment, in particular by virtue of the combination of criteria cooperating synergistically, the most suitable umbilical cord blood preparation, or other biological preparation, can be identified in a given stock and prepared for shipment. Advantageously, the process of selecting the preparation is automated. Thus, it is possible to standardize and speed up the time-consuming manual selection process which currently represents the key vulnerability in the supply chain of umbilical cord blood preparations.

It is also preferred to use and individually weight the following classification criteria and/or exclusion criteria:
- Preparations having a CD34+ cell count above 10% of the TNC count
- Exclusion of preparations wherein less than 75% of the CD34+ cells survived and/or were activated in a CA (colony assay)
- Blood group identity
- Ethnic identity
- Gender
- Age of preparation
- Accreditation standard
- Ranking of the UCB bank The preferred embodiment can ensure optimum quality of the preparations, thereby allowing successful transplantation. Advantageously, preparations having a CD34+ cell count above 10% of the TNC count are weighted differently to this end. Preparations wherein less than 75% of the CD34+ cells survived and/or were activated in the CA (Colony assay) are excluded so as to ensure a high number of hematopoietic stem cells. Similarly, this applies to CD133+ cells. Other criteria such as blood group identity, ethnic identity and gender can further circumscribe the selection of a preparation. Furthermore, old preparations can be excluded by determining the age of the preparation, so that only those preparations not having exceeded a defined age are advantageously used for transplantation, thereby ensuring surprisingly high quality. The accreditation standard ranking of the UCB bank can also be considered for selection. In this way, banks having e.g. little experience in storage or transplantation of umbilical cord blood can be excluded. The combination of classification and/or exclusion criteria allows qualitative characterization of the preparations, thereby reducing rejection of the preparations in transplantation and ensuring that a patient receives the "best", i.e. the best tolerated, preparation.

Advantageously, it is possible to establish selection criteria that can facilitate the search for a suitable preparation and also simplify the selection of a preparation. To this end, it is also possible to use information relating to the reliability and delivery speed of the UCB, which information is automatically collected by the system.

Depending on the clinic policy, these additional classification criteria can be assigned once or re-prioritized in particular cases. Prioritization will decide the fine selection in the final ranking of the preparations for possible solutions.

It is also preferred to use the preferred embodiment for allocating double or multiple transplantations (multi-cord). In this way, it is possible depending on the required number of cells to carry out double or multiple transplantations. That is, if a patient requires more cells than a suitable preparation can provide, an additional suitable preparation can be searched automatically.

Furthermore, the selection of multi-cord preparations is preferably performed according to the following classification criteria:

$ML_{P1P2}$=mutual compatibility of 2 preparations:

$$ML_{P1P2} := \begin{cases} 6: HLA_{Prep1} \text{ and } HLA_{Prep2} \text{ match in 6 out of 6} \\ \quad \text{values and blood group compatibility} \\ 5: HLA_{Prep1} \text{ and } HLA_{Prep2} \text{ match in 5 out of 6} \\ \quad \text{values and blood group compatibility} \\ 4: HLA_{Prep1} \text{ and } HLA_{Prep2} \text{ match in 4 out of 6} \\ \quad \text{values and blood group compatibility} \\ \text{Preparation not included: other} \end{cases}$$

$BL_{Multi}$=basic list to determine the selection list for multiple preparations:

$$BL_{Multi} := \left\{ p \in Prep \, \middle| \, \frac{CN_p}{BW_{Pat}} < \frac{1}{\text{kg}} \wedge ML_{Prep} \geq 4 \right\}$$

$SL_{multi}$=short list of preparations to be included in multiple transplants $$SL_{Multi} := \left\{ p1 \in BL_{Multi}, p2 \in BL_{Multi} \, \middle| \, ML_{p1p2} \geq 4 \wedge \frac{CN_{p1} + CN_{p2}}{BW_{Pat}} \geq 1 \right\}$$

The preferred embodiment provides a second part of the short list, i.e. the multi-cord view with matched preparations. Advantageously, already the suitability of different preparations with respect to each other is defined, so that, advantageously, there are no incompatibilities between multiple preparations administered to the patient. Advantageously, the short list includes preparations previously not considered alone or in combination, so that the required number of cells is either achieved or even surpassed. In multi-cord preparations the (partial) preparation having the higher CD34+ cell count is regarded as advantageous (the "first"). A preliminary budget for each single-cord and multi-cord appears on the short list, which calculates the cost of a preparation according to standard values in accordance with the status of said preparation. It may also be advantageous to select the multi-cord preparations on the basis of genome, proteome, transcriptome, epigenome and/or metabolome data. The preparations are characterized by performing genome, proteome, transcriptome, epigenome and/or metabolome analyses and entering the data into the system. This allows detailed characterization of the preparations and compatibility assessment of the preparations by means of the system. Surprisingly, it was found that such a characterization can significantly reduce the number of rejection responses.

Advantageously, the search results can be represented in a "compare view" including up to four preparations which can be compared with the patient data in a straightforward manner. The "compare view" compares all data of the unit report with the data of the patient.

The last step of the selection process involves proposed solutions advantageously presented to the attending physician in a clear and concise manner. Advantageously, the proposals comprise single preparations and/or multi-cord preparations. If and what type of single-cord or multi-cord is used is the final decision of the physician.

Advantageously, a folder/file including four sheets can be created for each proposed solution. This file is a working and communication tool for the cooperation between coordinator and attending physician or with respect to patient and clinic administration.

For example, said folder can be structured as follows:
Sheet 1 can be a worksheet or control slip showing the preparation(s) beside the patient data and illustrating the required subsequent steps to be processed until the point of transplantation. This involves in particular the requirements of HR typing, DNA samples, CAs, genome, proteome, transcriptome, epigenome and/or metabolome analyses, but also direct communication with the respective UCB bank, reservations up to binding purchase orders, shipment logistics and accounting up to delivery to the hospital administration.
Sheet 2 of the proposed solution may include the complete unit report(s).
Sheet 3 of the proposed solution can be used to document the decision; it summarizes the decision criteria of the physician, notes the final budget, and is signed by the physician. The physician can use this sheet to point to other proposed solutions to be used alternatively if the desired proposal cannot or no longer be implemented due to particular events.
Sheet 4 may comprise a clear description relating to the preparation, temporal course, and transplantation in general, which is available to the physician for patient information or to the patient.

Furthermore, if the first solution cannot be achieved (e.g. shipping damage or loss of a preparation from the first solution), proposed solutions can advantageously be documented in an annex to the file.

The sheets of the proposed solution are available to the hospital for the further course such as accounting and tracking of a transplantation, e.g. patient's medical history, and passed on to the respective UCB bank(s) at the appropriate time.

During the entire course and up to the aftercare of the patient, data of newly registered UCB preparations are advantageously transmitted to the clinic automatically and evaluated in terms of ranking on the long list and short list as well as proposed solutions.

This ensures dynamic improvement of proposed solutions and subsequent treatment of a patient on the basis of the latest data inventory.

In a preferred embodiment, a cell preparation suitable for allogeneic transplantation is selected. In allotransplantation, the transplanted tissue is not derived from the recipient but from a donor of the same biological species. To avoid serious or fatal rejection of foreign tissue, preferably complete matching of features recognized by the immune system with the host tissue is required for successful allogeneic transplantation. It was found advantageous to this end to perform a genome, proteome, transcriptome, epigenome and/or metabolome analysis. Preparation and recipient are characterized in detail by such high-resolution analyses, and the system can detect and avoid incompatibilities not detectable by standard methods (e.g. blood analysis). On the basis of preset parameters, it is possible by means of the preferred embodiment to perform an easy, rapid and advantageously automated search for a suitable, i.e. matching, preparation, so that—quite surprisingly—the risk of rejection is minimized and successful transplantation is not obstructed in any way.

In another preferred embodiment, an automatic and full-range selection of single-cord or multi-cord transplants is performed, wherein appropriate preparations are proposed to the attending physician and/or the coordinator, which preparations match in their parameters and do not generate any rejection responses. Advantageously, preparations matching each other and the patients are appropriately displayed so as to substantially facilitate and speed up the selection. The attending physician can therefore receive a representation of the two choices and come to an own judgment as to whether a multi-cord or single-cord transplantation should be performed. Surprisingly, automatic selection can avoid errors, and single-cord or multi-cord transplants can be presented to the attending physician. Advantageously, the presentation proceeds in a clear and concise manner, thereby facilitating the selection of preparations by the physician.

The search criteria are preferably adapted to the entered criteria and/or parameters. The current typing status of the UCBP is taken into account when selecting a suitable preparation. For example, this implies an assessment as to which additional investigations comprising genome, proteome, transcriptome, epigenome and/or metabolome analyses etc. are necessary so that the preparation can be confirmed as suitable and can be transplanted. To this end, the preferred embodiment preferably utilizes automatically collected statistics on expected cost and required time. In the event of time-critical scenarios, in particular, this is absolutely necessary and substantially speeds up the selection process. In general, the extensibility of the data scheme of UCBP and patient is advantageous in that additional search criteria can be adapted to a future state of the art.

It is also preferred that a matrix is used to display the results obtained using the search criteria and that the results are visually displayed. To this end, the preferred embodiment provides a visual guide as to the best search results according to the currently selected search parameters. To this end, the search results are arranged in a matrix and visualized. The matrix can be rearranged dynamically according to various criteria. Matching with respect to preset search criteria is displayed in colors. In the meaning of the invention the matrix can be described as a heat map wherein data of a parameter are displayed as colors in a two-dimensional representation.

It is also preferred that statistics relating to the expected cost and required time are used to assess the status of the determination of classification criteria. Advantageously, statistics relating to the search for a suitable preparation can be used for the determination of classification criteria. For example, this may include the expected costs, required time, successful transplantations of a hospital, and investigations in selecting a preparation still to be performed or in the classification assumed by a preparation. This allows preparations to be assessed more quickly and arranged accordingly. In addition, cost- and time-saving search is possible.

Thus, automatic and complete proposals of solutions for single-cord or multi-cord transplants can be developed. Advantageously, coordinator and physician can focus on the suitability of various well-defined and well-documented proposals of solutions. In a preferred fashion, coordination between hospital, transplant center and attending physician is carried out by means of the preferred embodiment. This ensures reliable communication between the hospital, i.e. optionally the attending physician, and the transplant center. Search parameters and results are presented in a clear and concise manner, thereby substantially facilitating the selection. Also, the parameters forming the basis of the search are variable and can be adapted to the patient and/or the desired preparation. This is a great improvement over the current situation in which coordinators are obliged to assess potential transplants at a very early stage according to various criteria. At present, this leads to unsatisfactory results and is exceedingly time-consuming and labor-intensive. Thus, the preferred embodiment allows searching and ordering one or more suitable preparations within a short period of time.

The invention will be explained below by way of example, but is not limited to the examples.

EXAMPLE 1

Prophylactic Health Strategies for Individuals and Families

Anne K. has ordered a genome analysis from a genotyping provider (e.g. 23andme). She receives the information that she has a strong genetic predisposition to leukemia and stroke. Anne K. then inquires via the system whether a genetically matching preparation has been stored and, if so, in which cord blood bank. In parallel, she inquires via the system with Bone Marrow Donors Worldwide (BMDW), Leiden, Germany, if a suitable donor is available. Using the system, she has booked the service of further inquiries, so that she or her account in the genotyping service provider will be informed about the status of suitable preparations or donors in the future at regular intervals. She can grant her physician access to this account/status at any time. In cases of emergency, this ensures rapid and reliable retrieval of a suitable preparation or donor via the system.

Moreover, Anne K. plans to collect umbilical cord blood each time she gives birth to a child. She may ask for autologous storage of these preparations at her own expense. Since autologous storage appears too expensive to her, she can use the system to donate the umbilical cord blood preparations to banks connected to the system, which banks guarantee that, in return for the donation, she, the father of the child or children, the siblings of the child or children would be given back the preparation for defined diseases and free of charge upon request of a treating physician, or, if sold, receive a free replacement preparation for the family.

Owing to the system, "health strategies" for individuals or families aware of genetic predispositions to certain diseases are possible for the first time. As a result of such behavior, Anne K. is able to negotiate benefits with her insurance.

EXAMPLE 2

Specific Storage of Umbilical Cord Blood Preparations Having Specific HLA and Other Characteristics A cord blood bank or a bone marrow register is connected to the system.

For example, the bank or the register increasingly receives inquiries for certain HLA types, but is not able to be of service by itself, or only to a limited extent, or the inventory connected to the system includes insufficient quantities thereof. The bank, or the register, uses the system to prompt a specific query of customers of genotyping providers e.g. for specific HLA types with the request to register or, in the event of childbirth, donate the umbilical cord blood to a bank registered in the system, because there is a high probability, i.e. about 20%, that the umbilical cord blood matches the requested type (for further course, see Example 1). In this way, the system can specifically and systematically supplement the inventory of connected banks or registers.

Genotyping providers can offer specific HLA types on the "marketplace" of the system.

The invention will be exemplified with reference to the figures, but is not limited to the examples.

Figure 2:
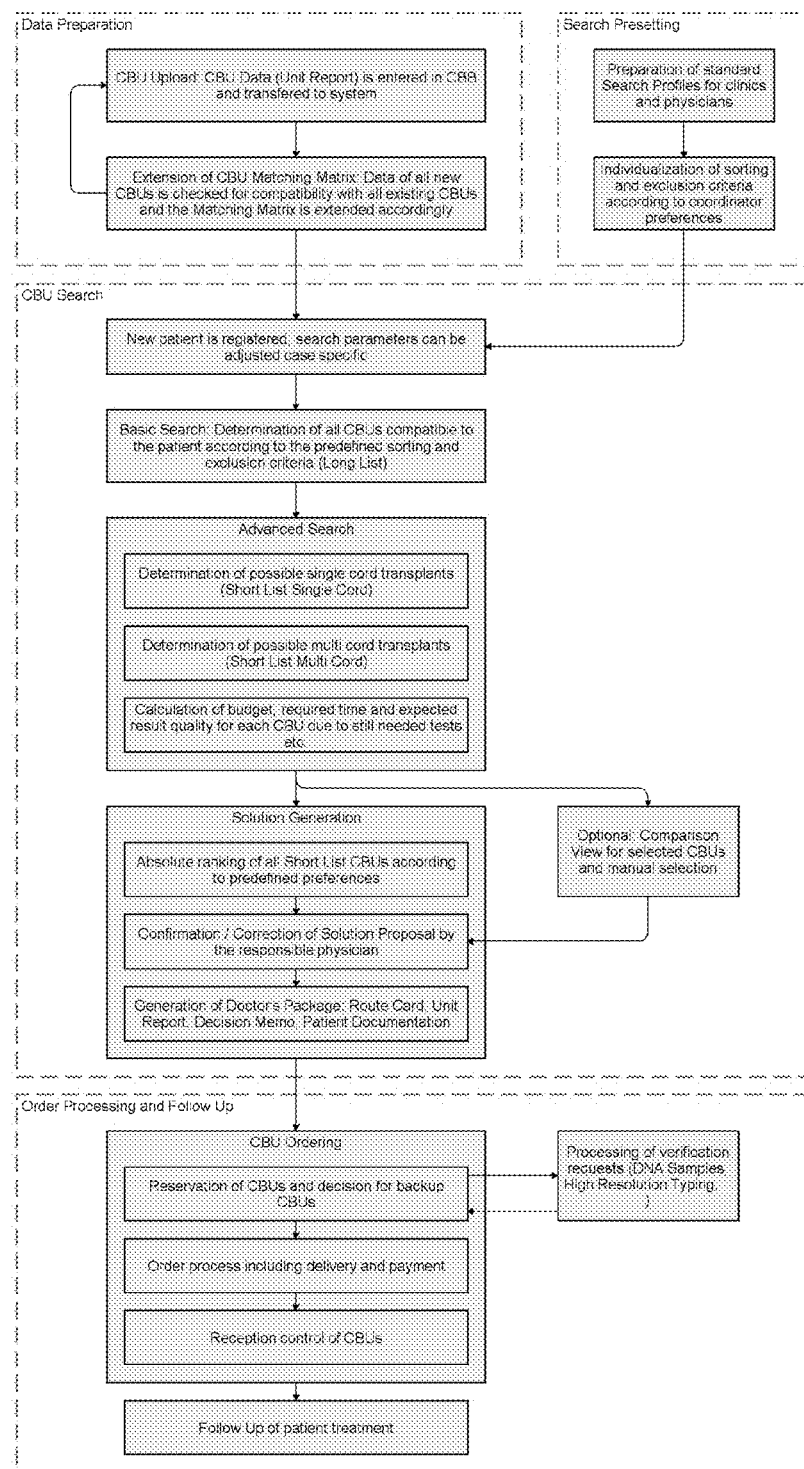
Figure 3:
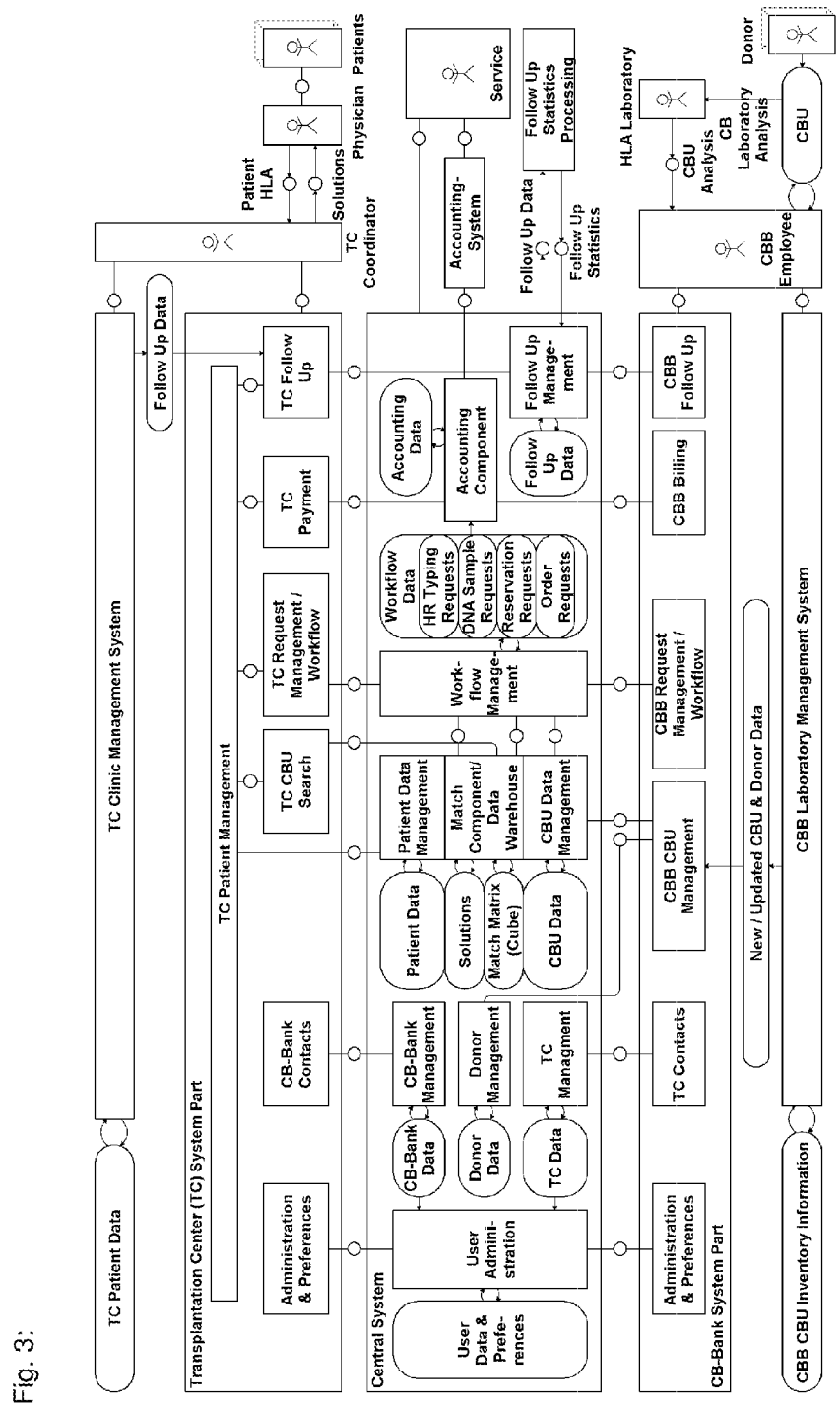
Figure 4:
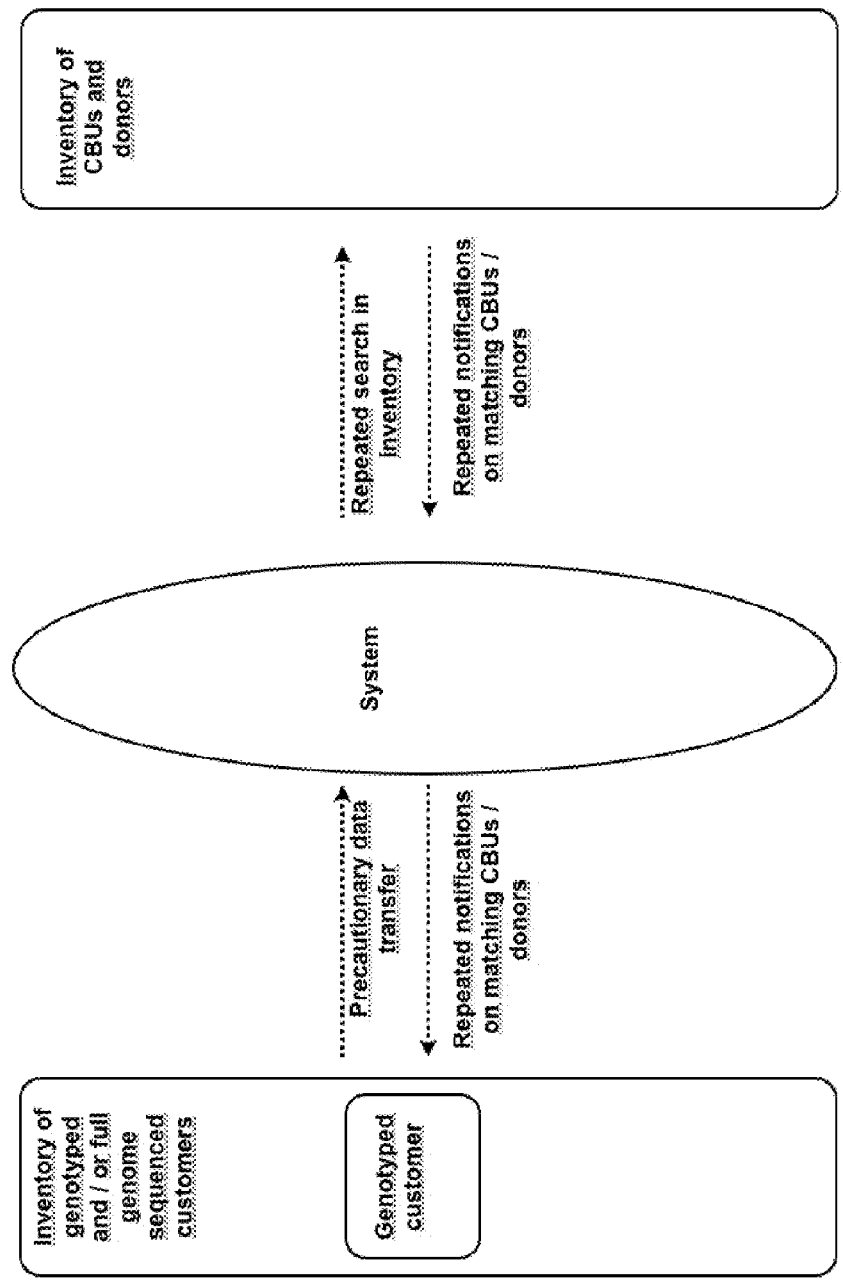
Figure 5:
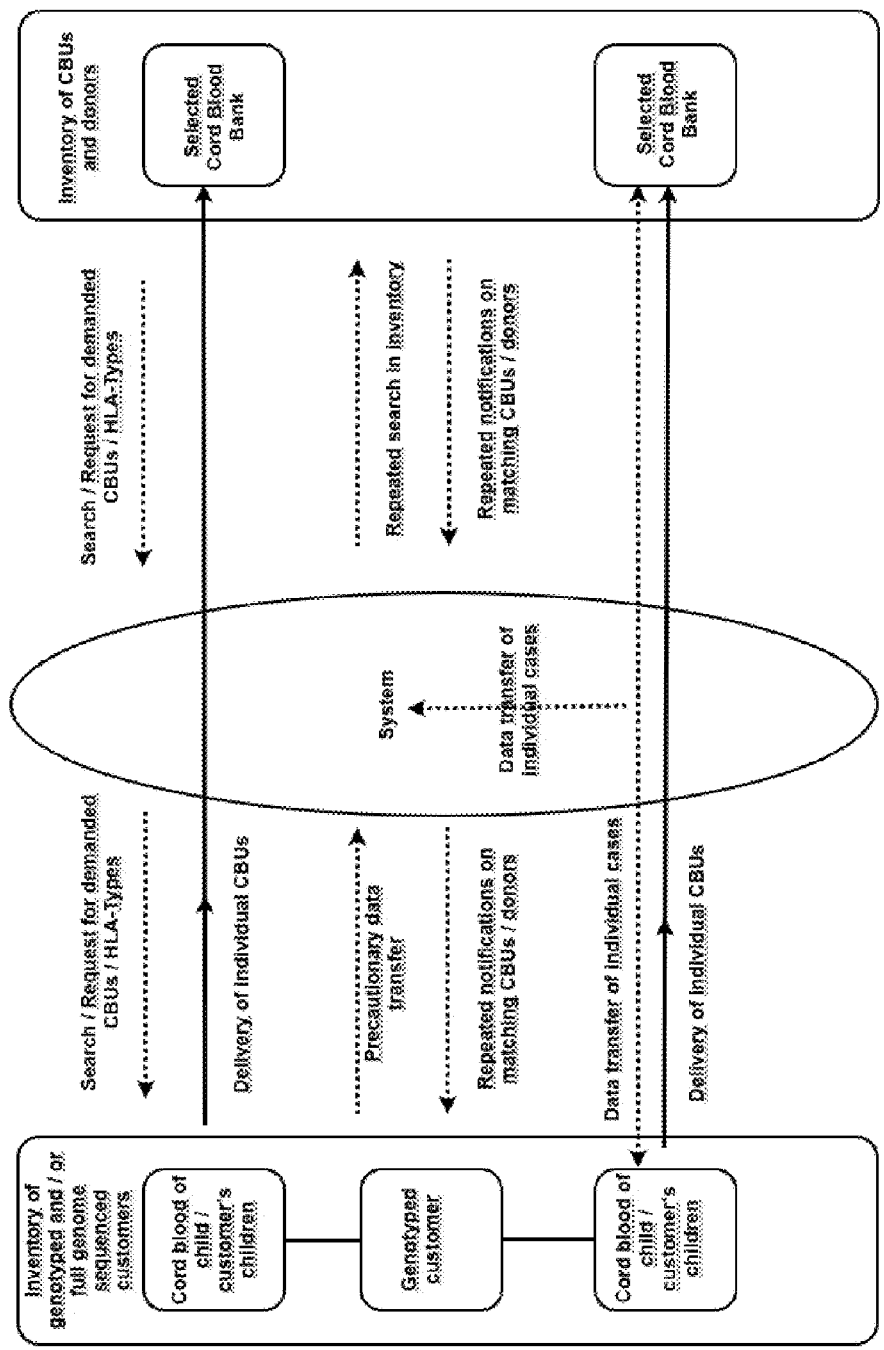

FIG. 1 shows the basic data model
FIG. 2 shows the process flow
FIG. 3 shows the system architecture
FIGS. 4 and 5 show the data transfer in the system FIG. 1 is an exemplary illustration of a preferred embodiment of the basic data model. In a first contact, the data of an individual, such as name, address and other contact information, can be recorded. For example, this may involve a UCB donor, in which event additional data can be input into the database (comprising maternity hospital and medical history of mother, father and/or child). Advantageously, the UCB bank data can also be collected and stored. Advantageous data comprise processing quality and a specific bank ID. The data of the UCB preparations advantageously comprise HLA type, TNC count, or viral status. This information can be used to accurately characterize a preparation, and additional details of the preparation can be determined using further tests (comprising high-resolution HLA typing or colony assays). Surprisingly, it was found that in particular genome, proteome, transcriptome, epigenome and/or metabolome analyses furnish comprehensive and detailed characterization of preparations. It is possible in this way to determine information comprising methylation status of defined genes, expression of biomarkers or gene/chromosome aberrations. Advantageously, a genome, proteome, transcriptome, epigenome and/or metabolome analysis of recipient, or potential recipient, and UCB preparation is carried out. The analyses can be used to calculate the compatibility of the system, and the results, i.e. the suitable preparations, are output hierarchically. The preparation is examined using the tests, and the quality can easily be assessed. Advantageously, the data of the preparation are compared with the data of a transplant patient, i.e. it is possible to compare e.g. blood group and urgency. Advantageously, it is also possible to analyze the genome, proteome, transcriptome, epigenome and/or metabolome data of the recipient, i.e. the patient. Based on this comparison, the preparation can advantageously be reserved for the patient by the transplant clinic. This can be done by a coordinator or an attending physician in the clinic. Advantageously, data of the hospital can be recorded and stored in a preferred database. These data comprise hospital ID or type of accreditation. Furthermore, the system allows monitoring of the transplantation by additionally performing genome, proteome, transcriptome, epigenome and/or metabolome analyses at preferably regular intervals after transplantation. It is possible in this way to precisely describe the course of the transplantation and detect complications at an early stage.

FIG. 2 is an exemplary illustration of the process flow. During data processing, new UCB preparations can be acquired in the UCB bank and imported into the preferred system. Advantageously, the newly acquired preparations can be compared for compatibility with UCB preparations present in the system. Advantageously, this can be effected via a compatibility matrix, for example. When searching a UCB preparation, the standard search profiles for hospitals and physicians can be used, in which event it is also possible with advantage to effect an individualization of classification and exclusion criteria according to coordination preference. Furthermore, the search for a UCB preparation suitable for a transplant patient can be adapted in a case-specific manner. It is possible to perform a so-called basic search wherein advantageously all patient-compatible UCB preparations are retrieved in accordance with preset classification and/or exclusion criteria (long list). Furthermore, it may be advantageous to perform a so-called advanced search wherein possible single transplants (single-cord) and/or multiple transplants (multi-cord) are determined. Advantageously, it is also possible to list the required budget, the time needed, and the quality of results per transplant on the basis of tests still to be performed. This involves a comparison of the retrieved preparations in a comparison view which also allows comparison of single preparations. Advantageously, a solution wherein the short list preparations are arranged according to predetermined references can be generated. In this way, a clear and concise representation of preparations can be presented to the attending physician, and the proposed solution being generated can advantageously be confirmed or corrected by the physician. The solution thus generated can be included in the medical record of the transplant patient, which comprises control slips, unit report, proposed decision, and patient documentation. Thus, all information relevant to UCB transplantation can advantageously be stored in a file. Once the transplant clinic, or the attending physician, has selected one or more UCB preparations, the preparation can be ordered from the UCB bank. Advantageously, the preparations retrieved by the search can be reserved for a patient or a clinic, and backup preparations can advantageously be determined in case the selected preparations are not available. Furthermore, additional verification (comprising DNA samples, high-resolution typing or genome, proteome, transcriptome, epigenome and/or metabolome analyses) can ensure the quality and compatibility of the preparations. Following selection, the preparations can be ordered and delivered. Advantageously, the preparations undergo a receiving control in the clinic. Advantageously, a patient follow-up is performed after successful transplantation.

FIG. 3 is an exemplary illustration of the preferred system architecture.

The illustration shows a schematic configuration of a preferred data-processing system component. The preferred embodiment of the system can be divided into three sections, i.e. central system, TC (transplant center) system component and umbilical cord blood bank (UCB bank) subsystem. Advantageously, the system can be used via internet and intranet, and the individual components can communicate and exchange data via wireless or wired connections. As demonstrated herein, UCB preparations can be supplied by donors and analyzed in an HLA laboratory. Analysis of the preparations by external service providers may also be preferred. For example, samples of UCB preparations can be shipped to the latter and genome, proteome, transcriptome, epigenome and/or metabolome analyses carried out. The data generated there are transmitted e.g. to the UCB bank and entered into the system and stored. Advantageously, the preparations can be physically processed and stored in the UCB bank, and the UCB preparation data obtained can advantageously be handled in the UCB bank in a laboratory management system. Details relating to selected UCB preparations can be transferred locally and incrementally into the central system, e.g. in the form of data sets. Advantageously, the preferred system provides the cord blood bank with the option of administration, inspection of communications of transplant center (TC) contacts, management of imported UCB preparations, comfortable processing of requests and workflow monitoring, management of complete accounting of UCB preparation supplies and services, and management of follow-up information. It may also be advantageous if the UCB bank communicates orders to collect samples, e.g. to the clinic, via the system. FIG. 3 also reveals that a physician can determine the HLA values of patients and pass them on together with further information e.g. to the TC coordinator for the search of UCB preparations. The coordinator can e.g. perform a system-based search and propose solutions and, advantageously, UCB preparations for transplantation. The patient data can be managed by the transplant center or by the hospital in a separate management system. Advantageously, follow-up information can be forwarded from there to the central system after transplantation. For example, the system can provide the transplant center with the option of administration, inspection of communications of UCB bank contacts, search for UCB preparations, comfortable commissioning and monitoring of requests and workflow monitoring, management of complete accounting of UCB preparation supplies and services, and management of follow-up information. Advantageously, the central system allows secure access to data deposited in encrypted from (e.g. in a database system) so as to ensure data security. Advantageously, the user data and settings thereof can be stored centrally so as to be available across sessions. Supervision of the central component (comprising set-up of new users, hospitals, UCB banks) can be performed by service personnel, for example. Information uploaded by the UCB bank can be supervised in the donor management and central UCB preparation management. The UCB data can be pre-arranged according to (e.g. modularly interchangeable) classification criteria (e.g. by means of a data warehouse cube) so as to ensure an advantageously rapid and efficient search even in the event of complex multiple transplantations. Advantageously, modularly different matching algorithms can be used in the matching component to generate appropriate solutions automatically or semi-automatically. All processes and interactions between the involved parties can be controlled by the workflow component. Furthermore, all transactions and services can be acquired and evaluated by the accounting component. Advantageously, processed accounting information can be transferred to an accounting system for e.g. rendering of accounts. The follow-up information can be supervised centrally and transferred to an external central department wherein e.g. follow-up statistics can be created and returned at regular intervals.

FIGS. 4 and 5 show a data transfer within the system. The system includes a stock of genotyped clients. The genome of a client or patient or recipient may have been sequenced or genotyped by a service provider, for example. It may also be preferred to enter and store genome, transcriptome, epigenome, proteome and/or metabolome data in the system. Using this data, e.g. a clinic can perform a detailed analysis and detect a predisposition to a disease. This can be effected on the basis of metabolic activities, epigenetic data, gene expression, proteome, and/or genome data. If a predisposition is present, an inquiry can be performed via the system whether a genetically matching preparation has been stored and, if so, in which cord blood bank. The system preferably also acquires other characteristics or features important to transplantation, comprising HLA values or blood type. Furthermore, the system can inquire with Bone Marrow Donors Worldwide if a suitable donor is possibly available. Advantageously, the system can automatically search for one or optionally more suitable preparations, i.e. the client or patient or potential recipient will be informed about the status of suitable preparations or donors in the future at regular intervals. It is also possible anytime to extend or reduce the number of participants having access to the system. Advantageously, this results in optimum communication between e.g. the hospitals and the UCB banks so that, on the one hand, the transplantation process can be made substantially more rapid and, on the other hand, multiple or double examinations can be avoided. The data of the participants are stored centrally or locally by the system and can be accessed by the participants. Advantageously, test results or high-throughput analyses optionally carried out by service providers are immediately stored in the system. The system can also store highly complex data, such as genome analyses, and use them in a search or analysis. A potential recipient, i.e. client, can rapidly and reliably retrieve a suitable preparation or donor via the system in cases of emergency. Furthermore, the system enables a potential recipient to have umbilical cord blood collected and autologously stored at each childbirth. In addition, the system can be used to donate UCB preparations to banks connected to the system, which banks guarantee the potential recipient that the preparation or a comparable replacement preparation is available to the potential recipient at any time.

It is also possible that a bank or register connected to the system increasingly receives inquiries for certain HLA types, which, however, cannot be accomplished or only to a limited extent. The system can then send a specific query to service providers offering genome, proteome, transcriptome, epigenome and/or metabolome analyses, the clients of which are registered by the system. Advantageously, further client data comprising HLA types or blood groups are available. These clients may optionally donate umbilical cord blood of a child. In this way, the system can specifically and systematically supplement the inventory of connected banks or registers with service providers offering genome, proteome, transcriptome, epigenome and/or metabolome analyses.

The invention claimed is:

1. A system for allocating and selecting umbilical cord blood preparations, for transplantations, therapies and/or research purposes, wherein the system comprises data processing equipment including one or more processing units connected via a network of said one or more processing units via which data is exchanged, wherein
said one or more processing units are configured to:
  store experience data of umbilical cord blood preparations imputed into a computer via one or more input devices,
  store inquiry data of a potential recipient or patient, said inquiry data comprising genome, transcriptome, proteome, epigenome and/or metabolome data,
  store preset search criteria,
  compare the experience data with the inquiry data, and automatically evaluate the search being effected, and/or
  effect order processing and tracking on the basis of this evaluation, the umbilical cord blood preparation being ordered via the network, and wherein
the one or more processing units are configured to arrange and select potential umbilical cord blood preparations according to HLA match, patient weight, number of nucleated cells (TNC) and number of hematopoietic cells (CD34+) and, in addition, compare them with said genome, transcriptome, proteome, epigenome and/or metabolome data,
wherein the one or more processing units are configured to execute a patient search that comprises determining patient-compatible preparations in accordance with the following classification and/or exclusion criteria:
  name and identification of clinic or transplantation center,
  names of coordinator and attending physician, including contact data,
  status of clinic with regard to international certifications (e.g. FACT),
  average number of UCB transplantations in the inquiring clinic during the last three years,
  name of patient, insurance number and other accounting information,
  patient's medical history,
  indication and therapy proposal of attending physician,
  urgency according to defined classification,
  HLA type of patient,
  blood group of patient,
  weight of patient,
  ethnic group of patient,
  sex of patient,
  age of patient,
  known allelic characteristics of patient and/or data of DNA typing, and/or
  first treatment or re-treatment,
said classification and/or exclusion criteria being stored on one of said processing units, and
wherein the one or more processing units are configured to produce short list(s) of potential umbilical cord preparations, using the following settings:

$$ML_{Prep} := \begin{cases} 6: HLA_{Prep} \text{ and } HLA_{Pat} \text{ match in 6 out of 6 typing values} \\ \qquad \text{and blood group compatibility} \\ 5: HLA_{Prep} \text{ and } HLA_{Pat} \text{ match in 5 out of 6 typing values} \\ \qquad \text{and blood group compatibility} \\ 4: HLA_{Prep} \text{ and } HLA_{Pat} \text{ match in 4 out of 6 typing values} \\ \qquad \text{and blood group compatibility} \\ \text{Preparation not included: other} \end{cases}$$

wherein $ML_{Prep}$=match level in accordance with HLA compatibility between preparation and patient, $$CF_{Prep} := \begin{cases} 3 \times 10^7 : ML_{Prep} = 6 \\ 4 \times 10^7 : ML_{Prep} = 5 \\ 5 \times 10^7 : ML_{Prep} = 4 \end{cases}$$

wherein $CF_{Prep}$=cell factor defining required number of cells per kg of patient weight at corresponding match level, $$CN_{Prep} := \frac{TNC_{Prep}}{CF_{Prep}}$$

wherein $CN_{Prep}$=classification number of a preparation allowing arrangement of preparations in accordance with TNC and match level, and wherein
the short list(s) of preparations to be considered for single transplants are produced using the following setting:

$$SL_{Single} := \left\{ p \in Prep \,\middle|\, \frac{CN_p}{BW_{Pat}} \geq \frac{1}{kg} \wedge ML_{Prep} \geq 4 \right\}$$

wherein $SL_{Single}$=short list of preparations (p) to be considered for single transplants,
and wherein standard classifications of preparations in the short list(s) are made according to the following criteria:
Classification 1=initial ranking according to match level, followed by classification number, followed by CD34+

$$\text{Classification 1 } (SL) := \begin{cases} p1 \in SL, \\ p2 \in SL \,\middle|\, \begin{array}{l} \text{either } ML_{p1} > ML_{p2} \\ \text{or } ML_{p1} = ML_{p2} \wedge CN_{p1} > CN_{p2} \\ \text{or } ML_{p1} = ML_{p2} \wedge CN_{p1} = CN_{p2} \wedge CD34_{p1}^+ \geq CD34_{p2}^+ \end{array} \end{cases}$$

and/or
Classification 2=initial ranking according to classification number, followed by match level, followed by CD34+

$$\text{Classification 2 } (SL) := \begin{cases} p1 \in SL, \\ p2 \in SL \,\middle|\, \begin{array}{l} \text{either } CN_{p1} > CN_{p2} \\ \text{or } CN_{p1} = CN_{p2} \wedge ML_{p1} > ML_{p2} \\ \text{or } CN_{p1} = CN_{p2} \wedge ML_{p1} = ML_{p2} \wedge CD34_{p1}^+ \geq CD34_{p2}^+ \end{array} \end{cases}$$

wherein
Prep=umbilical cord blood preparation,
Pat=patient,
$HLA_{Pat}$=HLA values of patient,
$HLA_{Prep}$=HLA values of preparation,
$TNC_{Prep}$=number of nucleated cells of preparation,
$BW_{Pat}$=body weight of patient in kg,
$CD34+_{Prep}$=number of CD34+ cells of a preparation, and
p1, p2=preparation 1 selected, preparation 2 selected.

2. The system according to claim 1,
wherein the one or more processing units are configured to
   acquire data regarding umbilical cord blood preparations with a data set during data processing, which data set comprises following parameters:
   name and identification of a UCB storage bank (UCB bank) of the preparation,
   status of the UCB storage bank with regard to international certifications, preferably FACT,
   process reliability of the UCB bank according to classification,
   contact in the respective bank, including contact data,
   identification number of preparation,
   medical history of mother, child and family according to anamnesis form of the maternity clinic,
   ethnic group of mother, father and/or child,
   sex of child,
   date of initial storage of preparation,
   details of preparation processing,
   blood group of preparation,
   HLA type of preparation,
   cell count (TNC) of preparation,
   cell count (CD34+) of preparation,
   viral status of preparation,
   allelic characteristics of preparation, and/or
   parameters of molecular diagnoses and analyses.

3. The system according to claim 1,
wherein
the genome data comprises sequenced chromosomes, genes and/or DNA of eukaryotes.

4. The system according to claim 1,
wherein
the transcriptome data comprises transcribed genes.

5. The system according to claim 1,
wherein
the proteome data comprises all proteins in a living organism, a tissue, a cell, or a cell compartment.

6. The system according to claim 1,
wherein
the metabolome data comprises flow rates or turnover rates, metabolite levels and enzyme activities of individual metabolic pathways and/or interactions between various metabolic pathways and/or compartmentalization of various metabolic pathways within a cell.

7. The system according to claim 1,
wherein
the epigenome data comprises all meiotically and mitotically heritable changes in gene expression that are not encoded in a DNA sequence.

8. The system according to claim 1, wherein
the following classification and/or exclusion criteria are used:
   preparations having a CD34+ cell count above 10% of the TNC count,
   exclusion of preparations wherein less than 75% of the CD34+ cells survived and/or were activated in a CA (colony assay),
   blood group identity,
   ethnic identity,
   gender,
   age of preparation,
   accreditation standard and/or
   ranking of the UCB bank.

9. The system according to claim 1,
wherein said one or more processing units are configured to allocate double or multiple transplantations (multi-cord).

10. The system according to claim 9,
wherein said one or more processing units are configured to perform the selection of multi-cord preparations according to the following classification criteria:

$$ML_{P1P2} := \begin{cases} 6: HLA_{Prep1} \text{ and } HLA_{Prep2} \\ \quad \text{match in 6 out of 6 typing values and blood group compatibility} \\ 5: HLA_{Prep1} \text{ and } HLA_{Prep2} \\ \quad \text{match in 5 out of 6 typing values and blood group compatibility} \\ 4: HLA_{Prep1} \text{ and } HLA_{Prep2} \\ \quad \text{match in 4 out of 6 typing values and blood group compatibility} \\ \text{Preparation not included: other} \end{cases}$$

wherein $ML_{P1P2}$=mutual compatibility of 2 preparations, and $$BL_{Multi} := \left\{ p \in Prep \,\Big|\, \frac{CN_p}{BW_{Pat}} < \frac{1}{\text{kg}} \wedge ML_{Prep} \geq 4 \right\}$$

wherein $BL_{Multi}$=basic list to determine the selection list for multiple preparations, and wherein said one or more processing units are configured to prepare a short list of preparations to be included in multiple transplants according to the following formula:

$$SL_{Multi} := \left\{ p1 \in BL_{Multi}, p2 \in BL_{Multi} \,\Big|\, ML_{p1p2} \geq 4 \wedge \frac{CN_{p1} + CN_{p2}}{BW_{Pat}} \geq 1 \right\},$$

$SL_{Multi}$=short list of preparations to be included in multiple transplants,
wherein
p1=preparation 1 selected,
p2=preparation 2 selected, and
Multi=multiple transplants.

11. A non-transitory computer-readable storage medium storing instructions that when executed by a computer cause the computer to perform a method for allocating and selecting umbilical cord blood preparations, the method comprising:
   accessing a storage medium of one or more processing units in which experience data of umbilical cord blood preparations from at least one collection center and/or storage site has been stored,
   inputting inquiry data of a potential recipient or patient and storing the data on said storage medium, said inquiry data comprising genome, transcriptome, proteome, epigenome and/or metabolome data at at least one clinic, transplant center and/or research facility,
   presetting search criteria on said storage medium,
   performing a search wherein the experience data is compared with inquiry data and performing an automatic evaluation of the search, and effecting order processing and tracking on the basis of this evaluation, and ordering the umbilical cord blood preparation via a network, wherein potential umbilical cord blood preparations are arranged and selected according to HLA match, patient weight, number of nucleated cells (TNC) and number of hematopoietic cells (CD34+), and compared with genome, transcriptome, proteome, epigenome and/or metabolome data, wherein said allocation and selection takes place between said least one collection center and/or storage site and said at least one clinic, transplant center and/or research facility, which communicate with each other via wired and/or wireless connections on one or more processing units, medical systems, storage devices and/or special processors and are connected via a network of said multiple processing units, medical systems, storage devices and/or special processors via which data are exchanged wherein the instructions case the computer to execute a patient search that comprises determining patient-compatible preparations in accordance with the following classification and/or exclusion criteria:

name and identification of clinic or transplantation center,
names of coordinator and attending physician, including contact data,
status of clinic with regard to international certifications (e.g. FACT),
average number of UCB transplantations in the inquiring clinic during the last three years,
name of patient, insurance number and other accounting information,
patient's medical history,
indication and therapy proposal of attending physician,
urgency according to defined classification,
HLA type of patient,
blood group of patient,
weight of patient,
ethnic group of patient,
sex of patient,
age of patient,
known allelic characteristics of patient and/or data of DNA typing, and/or
first treatment or re-treatment, said classification and/or exclusion criteria being stored on the computer-readable storage medium, and wherein the instructions case the computer is configured to produce short list(s) of potential umbilical cord preparations, using the following settings:

$ML_{Prep} :=$ $$\begin{cases} 6: HLA_{Prep} \text{ and } HLA_{Pat} \\ \quad \text{match in 6 out of 6 typing values and blood group compatibility} \\ 5: HLA_{Prep} \text{ and } HLA_{Pat} \\ \quad \text{match in 5 out of 6 typing values and blood group compatibility} \\ 4: HLA_{Prep} \text{ and } HLA_{Pat} \\ \quad \text{match in 4 out of 6 typing values and blood group compatibility} \\ \text{Preparation not included: other} \end{cases}$$

wherein $ML_{Prep}$=match level in accordance with HLA compatibility between preparation and patient, $$CF_{Prep} := \begin{cases} 3 \times 10^7 : ML_{Prep} = 6 \\ 4 \times 10^7 : ML_{Prep} = 5 \\ 5 \times 10^7 : ML_{Prep} = 4 \end{cases}$$

wherein $CF_{Prep}$=cell factor defining required number of cells per kg of patient weight at corresponding match level, $$CN_{Prep} := \frac{TNC_{Prep}}{CF_{Prep}}$$

wherein $CN_{Prep}$=classification number of a preparation allowing arrangement of preparations in accordance with TNC and match level, and wherein the short list(s) of preparations to be considered for single transplants are produced using the following setting:

$$SL_{Single} := \left\{ p \in Prep \,\middle|\, \frac{CN_p}{BW_{Pat}} \geq \frac{1}{\text{kg}} \wedge ML_{Prep} \geq 4 \right\}$$

wherein $SL_{Single}$=short list of preparations (p) to be considered for single transplants, and wherein standard classifications of preparations in the short list(s) are made according to the following criteria:

Classification 1=initial ranking according to match level, followed by classification number, followed by CD34+

$$\text{Classification 1}(SL) := \begin{cases} p1 \in SL, \\ p2 \in SL \,\middle|\, \begin{aligned} &\text{either } ML_{p1} > ML_{p2} \\ &\text{or } ML_{p1} = ML_{p2} \wedge CN_{p1} > CN_{p2} \\ &\text{or } ML_{p1} = ML_{p2} \wedge CN_{p1} = CN_{p2} \wedge CD34_{p1} \geq CD34_{p2} \end{aligned} \end{cases}$$

and/or

Classification 2=initial ranking according to classification number, followed by match level, followed by CD34+

$$\text{Classification 2}(SL) := \begin{cases} p1 \in SL, \\ p2 \in SL \,\middle|\, \begin{aligned} &\text{either } CN_{p1} > CN_{p2} \\ &\text{or } CN_{p1} = CN_{p2} \wedge ML_{p1} > ML_{p2} \\ &\text{or } CN_{p1} = CN_{p2} \wedge ML_{p1} = ML_{p2} \wedge CD34^+_{p1} \geq CD34^+_{p2} \end{aligned} \end{cases}$$

wherein
Prep=umbilical cord blood preparation,
Pat=patient,
$HLA_{Pat}$=HLA values of patient,
$HLA_{Prep}$=HLA values of preparation,
$TNC_{Prep}$=number of nucleated cells of preparation,
$BW_{Pat}$=body weight of patient in kg,
$CD34+_{Prep}$=number of CD34+ cells of a preparation, and
p1, p2=preparation 1 selected, preparation 2 selected.

* * * * *